United States Patent
Krushinski, Jr. et al.

(10) Patent No.: US 6,777,428 B1
(45) Date of Patent: Aug. 17, 2004

(54) 5-HT$_{1F}$ AGONIST

(75) Inventors: Joseph Herman Krushinski, Jr., Brownsburg, IN (US); Vincent Mancuso, Thy-le-Chateau (BE); Freddy Andre Napora, Gembloux (BE); John Mehnert Schaus, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/890,741
(22) PCT Filed: Feb. 9, 2000
(86) PCT No.: PCT/US00/02502
§ 371 (c)(1),
(2), (4) Date: Dec. 4, 2001
(87) PCT Pub. No.: WO00/47559
PCT Pub. Date: Aug. 17, 2000

Related U.S. Application Data

(60) Provisional application No. 60/119,596, filed on Feb. 10, 1999.

(51) Int. Cl.$^7$ .................. C07D 211/22; A61K 31/4465; A61K 31/445; A61K 31/454; A61P 25/06
(52) U.S. Cl. ................... 514/316; 514/326; 514/330; 546/189; 546/208; 546/225; 544/60; 544/130; 544/365
(58) Field of Search .................... 514/235.5, 227.8, 514/253.13, 316, 326, 330; 546/189, 208, 225; 544/60, 130, 365

(56) References Cited

U.S. PATENT DOCUMENTS

| | | | |
|---|---|---|---|
| 4,110,459 A | * 8/1978 | Helsley et al. | 514/323 |
| 5,118,689 A | * 6/1992 | Oinuma et al. | 514/300 |
| 5,254,689 A | * 10/1993 | Butera et al. | 544/360 |
| 5,286,866 A | * 2/1994 | Carr et al. | 546/225 |
| 5,708,008 A | 1/1998 | Audia et al. | 514/323 |
| 5,942,536 A | 8/1999 | Fritz et al. | 514/414 |
| 5,962,474 A | 10/1999 | Audia et al. | 514/323 |

FOREIGN PATENT DOCUMENTS

| | | |
|---|---|---|
| AU | A-33174/95 | 4/1996 |
| EP | 0 733 628 A | 9/1996 |
| EP | 0 832 650 A2 A3 | 4/1998 |
| WO | WO 95 00131 A | 1/1995 |
| WO | WO-97/08144 | 3/1997 |

OTHER PUBLICATIONS

Johnson, NeuroReport 8, 2237 (1997).*
Streitwiser, "Introduction to Organic Chemistry" (MacMillian, 1976) pag 586–587.*
Johnson, J. Neuroscinces Methods 81, 19–24 (1998).*
Adham N et al: "Cloning of Another Human Serotonin Receptor (5–HT1F): A Fifth 5–HT1Receptor Subtype Coupled to the Inhibition of Adenylate Cyclase" Proceedings of the National Academy of Sciences of USA, US, National Academy of Science. Washington, vol. 90, No. 2, Jan. 15, 1993 pp. 408–412, XP000572279.
Arch. Neurol. Psychiatry, 39:737–63, 1938 Oroham et al.
Cephalalgia, 12:5–7, 1992 Moskowitz.
Neurology, 43 (suppl. 3) :S16–S20 1993 Moskowitz.
Proc. Natl. Acad. Sci. USA, 90:408–412, 1993 Adham et al.
Adham N et al: "Cloning of Another Human Sertonin Receptor (5–HT1F): A Fifth 5–HT1Receptor Subtype Coupled to the Inhibition of Adenylate Cyclase" Proceedings of the National Academy of Sciences of USA, US, National Academy of Science. Washington, vol. 90, No. 2, Jan. 15, 1993 pp. 408–412, XP000572279.
Arch. Neurol. Psychlatry, 39:737–63, 1938.
Humphrey, et al., Ann. NY Acad. Sci., 600:587–600, 1900.
Cephalalgia, 12:5–7, 1992.
Neurology, 43 (suppl. 3) :S16–S20 1993.
Proc. Natl. Acad. Sci. USA, 90:408–412, 1993.

* cited by examiner

Primary Examiner—Mark L. Berch
(74) Attorney, Agent, or Firm—Robert Craig Tucker

(57) ABSTRACT

The present invention relates to a compound of formula I and a process for making:

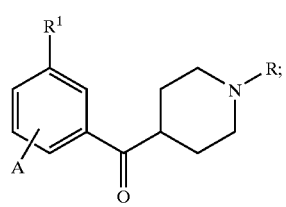

I or a pharmaceutical acid addition salt thereof; which are useful for activating 5-HT$_{1F}$ receptors and inhibiting neuronal protein extravasation in a mammal.

19 Claims, No Drawings

5-HT$_{1F}$ AGONIST

This U.S. national stage application of International Application PCT/US00/02502, filed Sep. 2, 2000, claims priority to U.S. provisional application Ser. No. 60/119,596, filed Feb. 10, 1999.

Theories regarding the pathophysiology of migraine have been dominated since 1938 by the work of Graham and Wolff. *Arch. Neurol. Psychiatry*, 39:737–63, 1938. They proposed that the cause of migraine headache was vasodilatation of. extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. Humphrey, et al., *Ann. NY Acad. Sci.*, 600:587–600, 1990. Recent work by Moskowitz has shown, however, that the occurrence of migraine headaches is independent of changes in vessel diameter. *Cephalalgia*. 12:5–7, 1992.

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology*, 43(suppl. 3):S16–S20 1993.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. *Proc. Natl. Acad. Sci. USA*, 90:408–412, 1993. This 5-HT$_{1F}$ receptor exhibits a pharmacological profile distinct from any serotonergic receptor yet described. The high affinity of sumatriptan at this subtype, K$_i$=23 nM, suggests a role of the 5-HT$_{1F}$ receptor in migraine.

This invention relates to novel 5-HT$_{1F}$ agonists which inhibit peptide extravasation due to stimulation of the trigeminal ganglia, and are therefore useful for the treatment of migraine and associated disorders.

The present invention relates to compounds of formula I:

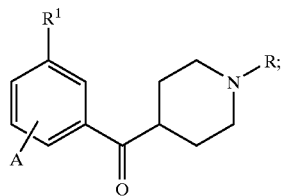

or a pharmaceutical acid addition salt thereof, where;

A is hydrogen, halo, —OR$^4$, NH$_2$, or —CF$_3$;

R is hydrogen, C$_1$–C$_4$ alkyl, C$_3$–C$_6$ alkenyl, C$_3$–C$_6$ alkynyl, or (C$_1$–C$_6$ alkyl)-Ar$^1$;

R$^1$ is —NH—R$^2$—R$^3$, hydroxy, —OSO$_2$Ar$^2$, or NH$_2$;

Ar, Ar$^1$, Ar$^2$, Ar$^3$, and Ar$^4$ are independently an optionally substituted phenyl or optionally substituted heteroaryl;

R$^2$ is —CO—, —CS—, or —SO$_2$—;

R$^3$ is hydrogen, optionally substituted C$_1$–C$_6$ alkyl, Ar$^3$, —NR$^5$R$^6$, or OR$^5$; provided R$^3$ is not hydrogen if R$^2$ is either —CS— or —SO$_2$—;

R$^4$ is hydrogen, optionally substituted C$_1$–C$_6$ alkyl, or Ar; and

R$^5$ and R$^6$ are independently hydrogen, optionally substituted C$_1$–C$_8$ alkyl, or Ar$^4$; or R$^6$ and R$^5$ combine, together with the nitrogen atom to which they are attached, to form a pyrrolidine, piperidine, piperazine, 4-substituted piperazine, morpholine or thiomorpholine ring.

This invention also relates to a pharmaceutical formulation comprising a compound of formula I, or a pharmaceutical acid addition salt thereof, and a pharmaceutical carrier, diluent, or excipient.

In addition, the present invention relates to a method for activating 5-HT$_{1F}$ receptors in mammals comprising administering to a mammal in need of such activation an effective amount of a compound of formula I, or a pharmaceutical acid addition salt thereof.

Moreover, the current invention relates to a method for inhibiting neuronal protein extravasation comprising administering to a mammal in need of such inhibition an effective amount of a compound of formula I, or a pharmaceutical acid addition salt thereof.

In addition, the present invention relates to a process for preparing the compounds of formula I(a):

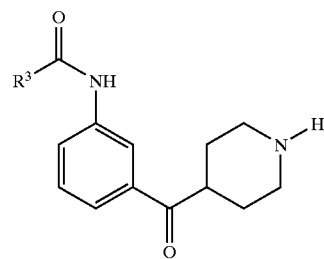

wherein R$^3$ is hydrogen, optionally substituted C$_1$–C$_6$ alkyl, Ar$^3$, —NR$^5$R$^6$, or OR$^5$;

R$^5$ and R$^6$ are independently hydrogen, optionally substituted C$_1$–C$_8$ alkyl, or Ar$^4$; or R$^6$ and R$^5$ combine, together with the nitrogen atom to which they are attached, to form a pyrrolidine, piperidine, piperazine, 4-substituted piperazine, morpholine or thiomorpholine ring; and Ar$^3$ and Ar$^4$ are independently an optionally substituted phenyl or optionally substituted heteroaryl, comprising:

(a) protecting 4-benzoylpiperidine hydrochloride to form an N-protected 4-benzoylpiperidine hydrochloride;

(b) nitrating the N-protected 4-benzoylpiperidine hydrochloride to form a mixture of N-protected 4-(mononitrobenzoyl)piperidines;

(c) deprotecting the N-protected 4-(mononitrobenzoyl) piperidine mixture to form a mixture of 4-(mononitrobenzoyl)piperidines;

(d) separating the 4-(3-nitrobenzoyl)piperidine from the mixture of 4-(mononitrobenz-oyl)piperidines;

(e) reducing the 4-(3-nitrobenzoyl)piperidine to form 4-(3-aminobenzoyl)piperidine; and (f) acylating the 4-(3-aminobenzoyl)piperidine.

One embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, chronic pain, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, allergic rhinitis, insect stings, trichotillomania, trigeminal neuralgia, dental pain or temperomandibular joint dysfunction pain. The compounds of this invention are also useful as a prophylactic treatment for migraine. Any of these methods employ a compound of formula I.

The use of a compound of formula I for the activation of the 5-HT$_{1F}$ receptor, for the inhibition of peptide extravasation in general or due to stimulation of the trigeminal ganglia specifically, and for the treatment of any of the disorders described above, are all embodiments of the present invention.

The general chemical terms used throughout have their usual meanings. For example, the term "$C_1$–$C_4$ alkyl" refers to methyl, ethyl, n-propyl, isopropyl, cyclopropyl, n-butyl, isobutyl, sec-butyl, tert-butyl and cyclobutyl. The term "$C_1$–$C_8$ alkyl" includes those groups listed for $C_1$–$C_4$ alkyl and also refers to saturated, straight, branched, or cyclic hydrocarbon chains of 5 to 8 carbon atoms. Such groups include, but are not limited to, pentyl, pent-2-yl, pent-3-yl, neopentyl, 2,3,4-trimethylpentyl, hexyl, hex-2-yl, hex-3-yl, hex-4-yl, 2,3-dimethylhexyl, 2-ethylhexyl, heptyl, hept-2-yl, hept-3-yl, hept-4-yl, octyl, oct-2-yl, oct-3-yl, oct-4-yl, oct-5-yl, and the like. The term "$C_3$–$C_8$ cycloalkyl" refers to cyclopropyl, cyclobutyl, cyclopentyl, cyclohexyl, cycloheptyl, and cyclooctyl.

The term "$C_3$–$C_6$ alkenyl" refers to mono-unsaturated straight or branched hydrocarbon chains containing from 3 to 6 carbon atoms and, includes, but is not limited to, allyl, 1-buten-4-yl, 2-buten-4-yl, 1-penten-5-yl, 2-penten-5-yl, 3-penten-5-yl, 1-hexen-6-yl, 2-hexen-6-yl, 3-hexen-6-yl, 4-hexen-6-yl and the like.

The term "$C_3$–$C_6$ alkynyl" refers to straight or branched hydrocarbon chains containing 1 triple bond and from 3 to 6 carbon atoms and includes, but is not limited to, propynyl, 2-butyn-4-yl, 1-butyn-4-yl, 1-pentyn-5-yl, 2-pentyn-5-yl and the like.

The terms "$C_1$–$C_6$ alkoxy" and "$C_1$–$C_4$ alkoxy" refer respectively to a $C_1$–$C_6$ alkyl and $C_1$–$C_4$ alkyl group bonded through an oxygen atom. The term "heteroaryloxy" refers to a heteroaryl or substituted heteroaryl group bonded through an oxygen atom. The term "aryloxy" refers to a phenyl or substituted phenyl group bonded through an oxygen atom. The term "$C_1$–$C_4$ acyl" refers to a formyl group or a $C_1$–$C_3$ alkyl group bonded through a carbonyl moiety. The term "$C_1$–$C_4$ alkoxycarbonyl" refers to a $C_1$–$C_4$ alkoxy group bonded through a carbonyl moiety.

The term "benzofused $C_4$–$C_8$ cycloalkyl" is taken to mean a $C_4$–$C_8$ cycloalkyl group fused to a phenyl ring. Examples of these groups include benzocyclobutyl, indanyl, 1,2,3,4-tetrahydronaphthyl, and the like.

The term "halo" includes fluoro, chloro, bromo and iodo.

The term "heterocycle" is taken to mean stable aromatic and non-aromatic 5- and 6-membered rings containing from 1 to 3 heteroatoms selected from the group consisting of nitrogen, oxygen and sulfur, said rings being optionally benzofused. All of these rings may be substituted with up to three substituents independently selected from the group consisting of halo, $C_1$–$C_4$ alkoxy, $C_1$–$C_4$ alkyl, cyano, nitro, hydroxy, —S(O)$_m$—($C_1$–$C_4$ alkyl) and —S(O)$_m$-phenyl where m is 0, 1 or 2. Non-aromatic rings include, for example, pyrrolidinyl, piperidinyl, piperazinyl, tetrahydrofuryl, oxazolidinyl, dioxanyl, pyranyl, and the like. Benzofused non-aromatic rings include indolinyl, 1,2,3,4-tetrahydroquinolinyl, 1,2,3,4-tetrahydroisoquinolinyl and the like. Aromatic rings include furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused aromatic rings include isoquinolinyl, benzoxazolyl, benzthiazolyl, quinolinyl, benzofuranyl, thionaphthyl, indolyl and the like.

The term "heteroaryl" is taken to mean an aromatic or benzofused aromatic heterocycle as defined in the previous paragraph.

The term "substituted $C_1$–$C_6$ alkyl" refers to a $C_1$–$C_6$ alkyl group that is substituted from 1 to 3 times independently with halo, hydroxy, phenyl, 2-phenylethylen-1-yl, diphenylmethyl, naphthyl, substituted phenyl, aryloxy, heterocycle, heteroaryloxy, $C_2$–$C_6$ alkenyl, $C_2$–$C_6$ alkynyl, $C_3$–$C_8$ cycloalkyl, $C_1$–$C_4$ alkoxy, $C_1$–$C_4$ alkoxycarbonyl, phenyl($C_1$–$C_4$ alkyl), substituted phenyl ($C_1$–$C_4$ alkyl), or benzofused $C_4$–$C_8$ cycloalkyl.

The terms "substituted phenyl" and "substituted phenyl ($C_1$–$C_4$ alkyl)" are taken to mean that the phenyl moiety in either case is substituted with one substituent selected from the group consisting of halo, nitro, cyano, amino, trifluoromethyl, trifluoromethoxy, phenyl, benzoyl, $C_1$–$C_6$ alkyl, $C_1$–$C_6$ alkoxy, ($C_1$–$C_4$ alkyl)S(O)$_n$ where n is 0, 1, or 2, ($C_1$–$C_4$ alkyl)$_2$ amino, $C_1$–$C_4$ acyl, or two to three substituents independently selected from the group consisting of halo, nitro, trifluoromethyl, $C_1$–$C_4$ alkyl, or $C_1$–$C_4$ alkoxy.

The term "substituted naphthyl" refers to a naphthyl group that may be substituted in the same manner as a substituted phenyl group.

The terms "substituted heteroaryl" and "substituted heteroaryl($C_1$–$C_4$ alkyl)" are taken to mean that the heteroaryl moiety in either case is substituted with up to three substituents independently selected from: halo, cyano, nitro, hydroxy, $C_1$–$C_4$ alkoxy, $C_1$–$C_4$ alkyl, ($C_1$–$C_4$ alkyl)-S(O)$_n$, and phenyl-S(O)$_n$; where n is 0, 1, or 2.

The term "amino protecting group" as used in this specification refers to a substituents commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivatized amino group is stable to the condition of subsequent reactions on other positions of the molecule and can be removed at the appropriate point without disrupting the remainder of the molecule. Further examples of groups referred to by the above terms are described by T. W. Greene, "Protective Groups in Organic Synthesis", John Wiley and Sons, New York, N.Y., 1991, Chapter 7 hereafter referred to as "*Greene*".

The term "pharmaceutical" when used herein as an adjective, means substantially non-toxic and substantially non-deleterious to the recipient.

By "pharmaceutical formulation" it is further meant that the carrier, solvent, excipients and salt must be compatible with the active ingredient of the formulation (a compound of formula I).

Since the compounds of this invention are amines, they are basic in nature and accordingly react with any of a number of inorganic and organic acids to form pharmaceutical acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature.

The term "acid, addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977.

The pharmaceutical acid addition salts of the invention are typically formed by reacting a compound of formula I with an equimolar or excess amount of acid. The reactants are generally combined in a mutual solvent such as diethylether, tetrahydrofuran, methanol, ethanol, isopropanol, benzene, ethyl acetate and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

The term "effective amount" means an amount of a compound of formula I which is capable of activating 5-HT$_{1F}$ receptors.

The term "suitable solvent" refers to any solvent, or mixture of solvents, inert to the ongoing reaction that sufficiently solubilizes the reactants to afford a medium within which to effect the desired reaction.

All enantiomers, diastereomers, and mixtures thereof, are included within the scope of the present invention. For example, when $R^1$ is NH—$R^2$—$R^3$; $R^2$ is —CO—; and $R^3$ is CH(OH)CH$_3$, the CH group of $R^3$ is a chiral center. Such centers are designed "R" or "S." For the purposes of the present application, the R and S enantiomers are illustrated below.

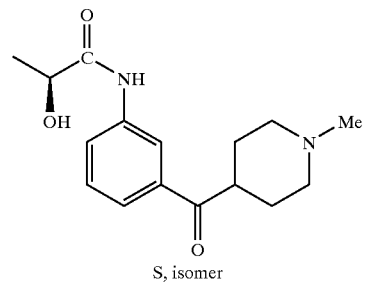

S, isomer

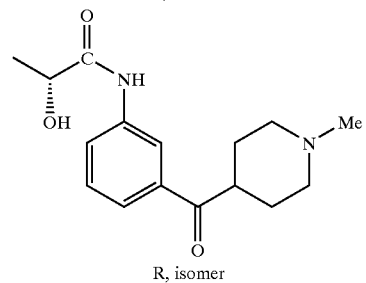

R, isomer

The following group is illustrative of compounds contemplated within the scope of this invention:

4-[3-((3-trifluoromethylphenyl)sulfonyloxy)benzoyl]-piperidine

4-[3-((4-trifluoromethoxyphenyl)sulfonyloxy)benzoyl]-1-methylpiperidine

4-[3-((3-bromophenyl)sulfonyloxy)benzoyl]-1-ethylpiperidine

4-[3-((3-trifluoromethoxyphenyl)sulfonyloxy)benzoyl]-1-propylpiperidine

4-[3-((4-chlorophenyl)sulfonyloxy)benzoyl]-1-butylpiperidine

4-[3-((2-hydroxyphenyl)sulfonyloxy)benzoyl]-1-pentenylpiperidine

4-[3-((4-bromophenyl) sulfonyloxy)benzoyl]-1-methylpiperidine

4-[3-((3,5-difluorophenyl)sulfonyloxy)benzoyl]-1-propenylpiperidine

4-[3-((3-methylphenyl)sulfonyloxy)benzoyl]-1-butenylpiperidine

4-[3-((pyrid-3-yl)sulfonyloxy)benzoyl]-1-methylpiperidine

4-[3-((pyrid-2-yl) sulfonyloxy)benzoyl]-1-methylpiperidine

4-[3-((2,3,4,5,6-pentafluorophenyl)sulfonyloxy)benzoyl]-1-hexenylpiperidine

4-[3-((4-methylphenyl)sulfonyloxy)benzoyl]-1-propynylpiperidine

4-[3-((3,4,5-trifluorophenyl)sulfonyloxy)benzoyl]-1-butynylpiperidine

4-[3-((2,3,4,5-tetrafluorophenyl)sulfonyloxy)benzoyl]-1-pentynylpiperidine

4-[3-((2-trifluoromethylphenyl)sulfonyloxy)benzoyl]-1-hexynylpiperidine

4-[3-((4-fluorophenyl)sulfonyloxy)benzoyl]-1-(phenylmethyl)piperidine

4-[3-((3-chlorophenyl)sulfonyloxy)benzoyl]-1-(phenylethyl)piperidine

4-[3-((4-iodophenyl)sulfonyloxy)benzoyl]-1-methylpiperidine

4-[3-((3-fluorophenyl)sulfonyloxy)benzoyl]-1-(2-phenylpropyl)piperidine
4-[3-((4-methoxyphenyl)sulfonyloxy)benzoyl]-1-(pyrrolidin-2-ylmethyl)piperidine
4-[3-((2-methylphenyl)sulfonyloxy)benzoyl]-1-(piperidin-1-ylethyl)piperidine
4-[3-((4-nitrophenyl)sulfonyloxy)benzoyl]-1-methylpiperidine
4-[3-((2,3-difluorophenyl)sulfonyloxy)benzoyl]-1-(piperazin-2-ylpropyl)piperidine
4-[3-((fur-2-yl)sulfonyloxy)benzoyl]-1-methylpiperidine
4-[3-((thiophen-2-yl)sulfonyloxy)benzoyl]-1-methylpiperidine
4-[3-((2,3,4-trifluorophenyl)sulfonyloxy)benzoyl]-1-(thien-2-ylmethyl)piperidine
4-[3-((pyridin-4-yl)sulfonyloxy)benzoyl]-1-methylpiperidine
4-[3-((4-cyanophenyl)sulfonyloxy)benzoyl]-1-methylpiperidine
4-[3-((3,4-difluorophenyl)sulfonyloxy)benzoyl]-1-(dioxan-2-ylmethyl)piperidine
4-[3-((2-fluorophenyl)sulfonyloxy)benzoyl]-1-methylpiperidine
4-[3-((2-trifluoromethoxyphenyl)sulfonyloxy)benzoyl]-1-methylpiperidine
4-[3-((4-fluorophenyl)sulfonyloxy)benzoyl]-1-methylpiperidine hydrochloride
4-[3-(phenylsulfonyloxy)benzoyl]-1-methylpiperidine
4-[3-((2-bromophenyl)sulfonyloxy)benzoyl]-1-methylpiperidine
4-[3-((2,3,5-trifluorophenyl)sulfonyloxy)benzoyl]-1-methylpiperidine hydrobromide
4-[3-((2-nitrophenyl)sulfonyloxy)benzoyl]-1-methylpiperidine
4-[3-((2,4,5-trifluorophenyl)sulfonyloxy)benzoyl]-1-methylpiperidine sulfide
4-[3-((2-iodophenyl)sulfonyloxy)benzoyl]-1-methylpiperidine
4-[3-(3-nitrophenylthioureido)benzoyl]-1-methylpiperidine
4-[3-(3-trifluoromethylphenylthioureido)benzoyl]-1-methylpiperidine oxalate
4-[3-(4-trifluoromethoxyphenylthioureido)benzoyl]-1-methylpiperidine methanesulfonate
4-[3-(phenylthioureido)benzoyl]-1-methylpiperidine
4-[3-(3-bromophenylthioureido)benzoyl]-1-methylpiperidine
4-[3-(3-trifluoromethoxyphenylthioureido)benzoyl]-1-methylpiperidine fumarate
4-[3-(4-chlorophenylthioureido)benzoyl]-1-methylpiperidine
4-[3-(2-hydroxyphenylthioureido)benzoyl]-1-methylpiperidine
4-[3-(4-bromophenylthioureido)benzoyl]-1-methylpiperidine
4-[3-(3,5-difluorophenylthioureido)benzoyl]-1-methylpiperidine phthalate
4-[3-(3-methylphenylthioureido)benzoyl]-1-methylpiperidine
4-[3-(pyrid-3-ylthioureido)benzoyl]-1-methylpiperidine
4-[3-(pyrid-2-ylthioureido)benzoyl]-1-methylpiperidine
4-[3-(2,3,4,5,6-pentafluorophenylthioureido)benzoyl]-1-methylpiperidine chlorobenzoate
4-[3-(4-methylphenylthioureido)benzoyl]-1-methylpiperidine
4-[3-(3,4,5-trifluorophenylthioureido)benzoyl]-1-methylpiperidine citrate
4-[3-(2,3,4,5-tetrafluorophenylthioureido)benzoyl]-1-methylpiperidine tartrate
4-[3-(2-trifluoromethylphenylthioureido)benzoyl]-1-methylpiperidine propanesulfonate
4-[3-(4-fluorophenylthioureido)benzoyl]-1-methylpiperidine
4-[3-(3-chlorophenylthioureido)benzoyl]-1-methylpiperidine
4-[3-(4-iodophenylthioureido)benzoyl]-1-methylpiperidine
4-[3-(3-fluorophenylthioureido)benzoyl]-1-methylpiperidine
4-[3-(4-methoxyphenylthioureido)benzoyl]-1-methylpiperidine
4-[3-(2-methylphenylthioureido)benzoyl]-1-methylpiperidine
4-[3-(4-nitrophenylthioureido)benzoyl]-1-methylpiperidine
4-[3-(2,3-difluorophenylthioureido)benzoyl]-1-methylpiperidine hydroxybenzoate
4-[3-(fur-2-ylthioureido)benzoyl]-1-methylpiperidine
4-[3-(thiophen-2-ylthioureido)benzoyl]-1-methylpiperidine
4-[3-(2,3,4-trifluorophenylthioureido)benzoyl]-1-methylpiperidine decanoate
4-[3-(pyridin-4-ylthioureido)benzoyl]-1-methylpiperidine
4-[3-(4-cyanophenylthioureido)benzoyl]-1-methylpiperidine
4-[3-(3,4-difluorophenylthioureido)benzoyl]-1-methylpiperidine monohydrogenphosphate
4-[3-(2-fluorophenylthioureido)benzoyl]-1-methylpiperidine
4-[3-(2-trifluoromethoxyphenylthioureido)benzoyl]-1-1-methylpiperidine sulfite
4-[3-(4-fluorophenylthioureido)benzoyl]-1-methylpiperidine
4-[3-(2-bromophenylthioureido)benzoyl]-1-methylpiperidine
4-[3-(2,3,5-trifluorophenylthioureido)benzoyl]-1-methylpiperidine pyrosulfate
4-[3-(2-nitrophenylthioureido)benzoyl]-1-methylpiperidine
4-[3-(2,4,5-trifluorophenylthioureido)benzoyl]-1-ethylpiperidine malonate
4-[3-(2-iodophenylthioureido)benzoyl]-1-methylpiperidine
4-[3-(3-nitrophenylureido)benzoyl]-1-methylpiperidine
4-[3-(3-trifluoromethylphenylureido)benzoyl]-1-methylpiperidine xylenesulfonate
4-[3-(4-trifluoromethoxyphenylureido)benzoyl]-1-propylpiperidine glycollate
4-[3-(phenylureido)benzoyl]-1-methylpiperidine
4-[3-((+)-2-hydroxypropylureido)benzoyl]-1-methylpiperidine 4-[3-((−)-3-phenylbutylureido)benzoyl]-1-methylpiperidine
4-[3-(R-2-(diphenylmethyl)propylureido)benzoyl]-1-methylpiperidine
4-[3-(S-2-hydroxypropylureido)benzoyl]-1-methylpiperidine
4-[3-(3-trifluoromethoxyphenylureido)benzoyl]-1-methylpiperidine lactate
4-[3-(4-chlorophenylureido)benzoyl]-1-methylpiperidine
4-[3-(2-hydroxyphenylureido)benzoyl]-1-methylpiperidine
4-[3-(4-bromophenylureido)benzoyl]-1-methylpiperidine
4-[3-(3,5-difluorophenylureido)benzoyl]-1-methylpiperidine
4-[3-(3-methylphenylureido)benzoyl]-1-methylpiperidine
4-[3-(pyrid-3-ylureido)benzoyl]-1-methylpiperidine
4-[3-(pyrid-2-ylureido)benzoyl]-1-methylpiperidine
4-[3-(2,3,4,5,6-pentafluorophenylureido)benzoyl]-1-methylpiperidine mandelate
4-[3-(4-methylphenylureido)benzoyl]-1-methylpiperidine
4-[3-(3,4,5-trifluorophenylureido)benzoyl]-1-methylpiperidine lactate
4-[3-(2,3,4,5-tetrafluorophenylureido)benzoyl]-1-methylpiperidine caprylate
4-[3-(2-trifluoromethylphenylureido)benzoyl]-1-methylpiperidine acrylate
4-[3-(4-fluorophenylureido)benzoyl]-1-methylpiperidine
4-[3-(3-chlorophenylureido)benzoyl]-1-methylpiperidine
4-[3-(4-iodophenylureido)benzoyl]-1-methylpiperidine
4-[3-(3-fluorophenylureido)benzoyl]-1-methylpiperidine
4-[3-(4-methoxyphenylureido)benzoyl]-1-methylpiperidine
4-[3-(2-methylphenylureido)benzoyl]-1-methylpiperidine
4-[3-(4-nitrophenylureido)benzoyl]-1-methylpiperidine
4-[3-(2,3-difluorophenylureido)benzoyl]-1-methylpiperidine
4-[3-(fur-2-ylureido)benzoyl]-1-methylpiperidine
4-[3-(thiophen-2-ylureido)benzoyl]-1-methylpiperidine
4-[3-(2,3,4-trifluorophenylureido)benzoyl]-1-methylpiperidine formate
4-[3-(pyridin-4-ylureido)benzoyl]-1-methylpiperidine
4-[3-(4-cyanophenylureido)benzoyl]-1-methylpiperidine
4-[3-(3,4-difluorophenylureido)benzoyl]-1-methylpiperidine
4-[3-(2-fluorophenylureido)benzoyl]-1-methylpiperidine
4-[3-(2-trifluoromethoxyphenylureido)benzoyl]-1-methylpiperidine iodide
4-[3-(4-fluorophenylureido)benzoyl]-1-methylpiperidine
4-[3-(2-bromophenylureido)benzoyl]-1-methylpiperidine
4-[3-(2,3,5-trifluorophenylureido)benzoyl]-1-methylpiperidine
4-[3-(2-nitrophenylureido)benzoyl]-1-methylpiperidine
4-[3-(2,4,5-trifluorophenylureido)benzoyl]-1-methylpiperidine
4-[3-(2-iodophenylureido)benzoyl]-1-methylpiperidine
4-[3-(3-nitrophenylsulfonamino)benzoyl]-1-methylpiperidine
4-[3-(3-trifluoromethylphenylsulfonamino)benzoyl]-1-methylpiperidine
4-[3-(4-trifluoromethoxyphenylsulfonamino)benzoyl]-1-methylpiperidine
4-[3-(phenylsulfonamino)benzoyl]-1-methylpiperidine
4-[3-(3-bromophenylsulfonamino)benzoyl]-1-methylpiperidine
4-[3-(3-trifluoromethoxyphenylsulfonamino)benzoyl]-1-methylpiperidine
4-[3-(4-chlorophenylsulfonamino)benzoyl]-1-methylpiperidine
4-[3-(2-hydroxyphenylsulfonamino)benzoyl]-1-methylpiperidine
4-[3-(4-bromophenylsulfonamino)benzoyl]-1-methylpiperidine
4-[3-(3,5-difluorophenylsulfonamino)benzoyl]-1-methylpiperidine
4-[3-(3-methylphenylsulfonamino)benzoyl]-1-methylpiperidine
4-[3-(pyrid-3-ylsulfonamino)benzoyl]-1-methylpiperidine
4-[3-(pyrid-2-ylsulfonamino)benzoyl]-1-methylpiperidine
4-[3-(2,3,4,5,6-pentafluorophenylsulfonamino)benzoyl]-1-methylpiperidine
4-[3-(4-methylphenylsulfonamino)benzoyl]-1-methylpiperidine
4-[3-(3,4,5-trifluorophenylsulfonamino)benzoyl]-1-methylpiperidine
4-[3-(2,3,4,5-tetrafluorophenylsulfonamino)benzoyl]-1-methylpiperidine
4-[3-(2-trifluoromethylphenylsulfonamino)benzoyl]-1-methylpiperidine
4-[3-(4-fluorophenylsulfonamino)benzoyl]-1-methylpiperidine
4-[3-(3-chlorophenylsulfonamino)benzoyl]-1-methylpiperidine
4-[3-(4-iodophenylsulfonamino)benzoyl]-1-methylpiperidine
4-[3-(3-fluorophenylsulfonamino)benzoyl]-1-methylpiperidine
4-[3-(4-methoxyphenylsulfonamino)benzoyl]-1-methylpiperidine
4-[3-(2-methylphenylsulfonamino)benzoyl]-1-methylpiperidine
4-[3-(4-nitrophenylsulfonamino)benzoyl]-1-methylpiperidine
4-[3-(2,3-difluorophenylsulfonamino)benzoyl]-1-methylpiperidine
4-[3-(fur-2-ylsulfonamino)benzoyl]-1-methylpiperidine
4-[3-(thiophen-2-ylsulfonamino)benzoyl]-1-methylpiperidine
4-[3-(2,3,4-trifluorophenylsulfonamino)benzoyl]-1-methylpiperidine
4-[3-(pyridin-4-ylsulfonamino)benzoyl]-1-methylpiperidine
4-[3-(4-cyanophenylsulfonamino)benzoyl]-1-methylpiperidine
4-[3-(3,4-difluorophenylsulfonamino)benzoyl]-1-methylpiperidine
4-[3-(2-fluorophenylsulfonamino)benzoyl]-1-methylpiperidine 4-[3-(2-trifluoromethoxyphenylsulfonamino)benzoyl]-1-methylpiperidine
4-[3-(4-fluorophenylsulfonamino)benzoyl]-1-methylpiperidine
4-[3-(2-bromophenylsulfonamino)benzoyl]-1-methylpiperidine
4-[3-(2,3,5-trifluorophenylsulfonamino)benzoyl]-1-methylpiperidine
4-[3-(2-nitrophenylsulfonamino)benzoyl]-1-methylpiperidine
4-[3-(2,4,5-trifluorophenylsulfonamino)benzoyl]-1-methylpiperidine
4-[3-(2-iodophenylsulfonamino)benzoyl]-1-methylpiperidine
4-[3-((3-trifluoromethylphenyl)amidyl)benzoyl]-1-methylpiperidine
4-[3-((4-trifluoromethoxyphenyl)amidyl)benzoyl]-1-methylpiperidine
4-[3-((3-bromophenyl)amidyl)benzoyl]-1-methylpiperidine
4-[3-((3-trifluoromethoxyphenyl)amidyl)benzoyl]-1-methylpiperidine
4-[3-((4-chlorophenyl)amidyl)benzoyl]-1-methylpiperidine
4-[3-((2-hydroxyphenyl)amidyl)benzoyl]-1-methylpiperidine
4-[3-((4-bromophenyl)amidyl)benzoyl]-1-methylpiperidine
4-[3-(3,5-difluorophenyl)amidyl)benzoyl]-1-methylpiperidine
4-[3-((3-methylphenyl)amidyl)benzoyl]-1-methylpiperidine
4-[3-((pyrid-3-yl)amidyl)benzoyl]-1-methylpiperidine
4-[3-((pyrid-2-yl)amidyl)benzoyl]-1-methylpiperidine
4-[3-((2,3,4,5,6-pentafluorophenyl)amidyl)benzoyl]-1-methylpiperidine
4-[3-((4-methylphenyl)amidyl)benzoyl]-1-methylpiperidine
4-[3-((3,4,5-trifluorophenyl)amidyl)benzoyl]-1-methylpiperidine
4-[3-((2,3,4,5-tetrafluorophenyl)amidyl)benzoyl]-1-methylpiperidine
4-[3-((2-trifluoromethylphenyl)amidyl)benzoyl]-1-methylpiperidine
4-[3-((4-fluorophenyl)amidyl)benzoyl]-1-methylpiperidine
4-[3-((3-chlorophenyl)amidyl)benzoyl]-1-methylpiperidine
4-[3-((4-iodophenyl)amidyl)benzoyl]-1-methylpiperidine
4-[3-((3-fluorophenyl)amidyl)benzoyl]-1-methylpiperidine
4-[3-((4-methoxyphenyl)amidyl)benzoyl]-1-methylpiperidine
4-[3-((2-methylphenyl)amidyl)benzoyl]-1-methylpiperidine
4-[3-((4-nitrophenyl)amidyl)benzoyl]-1-methylpiperidine
4-[3-((2,3-difluorophenyl)amidyl)benzoyl]-1-methylpiperidine
4-[3-((fur-2-yl)amidyl)benzoyl]-1-methylpiperidine
4-[3-((thiophen-2-yl)amidyl)benzoyl]-1-methylpiperidine
4-[3-((2,3,4-trifluorophenyl)amidyl)benzoyl]-1-methylpiperidine
4-[3-((pyridin-4-yl)amidyl)benzoyl]-1-methylpiperidine
4-[3-((4-cyanophenyl)amidyl)benzoyl]-1-methylpiperidine
4-[3-((3,4-difluorophenyl)amidyl)benzoyl]-1-methylpiperidine
4-[3-((2-fluorophenyl)amidyl)benzoyl]-1-methylpiperidine
4-[3-((2-trifluoromethoxyphenyl)amidyl)benzoyl]-1-methylpiperidine
4-[3-((4-fluorophenyl)amidyl)benzoyl]-1-methylpiperidine
4-[3-(phenylamidyl)benzoyl]-1-methylpiperidine
4-[3-((2-bromophenyl)amidyl)benzoyl]-1-methylpiperidine
4-[3-((2,3,5-trifluorophenyl)amidyl)benzoyl]-1-methylpiperidine
4-[3-((2-nitrophenyl)amidyl)benzoyl]-1-methylpiperidine
4-[3-((2,4,5-trifluorophenyl)amidyl)benzoyl]-1-methylpiperidine While all enantiomers, diastereomers, and mixtures thereof, are useful as 5-HT$_{1F}$ agonists, single enantiomers and single diastereomers are preferred. Furthermore, while all of the compounds of this invention are useful as 5-HT$_{1F}$ agonists, certain classes are preferred. The following paragraphs describe such preferred classes.

1) R is hydrogen;
2) R is methyl;
3) R is [1-(isopropyl)pyrazol-4-yl]ethyl;
4) A is hydrogen;
5) A is 2-amino;
6) $R^1$ is —NH—$R^2$—$R^3$;
7) $R^1$ is hydroxy;
8) $R^1$ is —OSO$_2$R$^3$;
9) $R^1$ is NH$_2$;
10) $R^2$ is —CO—;
11) $R^2$ is —SO$_2$—;
12) $R^2$ is —CS—;
13) when $R^2$ is —SO$_2$—, $R^3$ is $C_1$–$C_6$ alkyl;
14) when $R^2$ is —SO$_2$—, $R^3$ is selected from the group consisting of methyl, butyl, isopropyl, and cyclohexyl;
15) when $R^2$ is —SO$_2$—, $R^3$ is phenyl;
16) when $R^2$ is —SO$_2$—, $R^3$ is monosubstituted phenyl;
17) when $R^2$ is —SO$_2$—, $R^3$ is selected from the group consisting of 4-iodophenyl, and 4-fluorophenyl;
18) when $R^2$ is —SO$_2$—, $R^3$ is 4-iodophenyl;
19) when $R^2$ is —CO— or —CS—, $R^3$ is —NR$^5$R$^6$;
20) when $R^2$ is —CO— and $R^3$ is NR$^5$R$^6$, $R^5$ and $R^6$ are hydrogen;
21) when $R^2$ is —CO— and $R^3$ is NR$^5$R$^6$, $R^5$ is hydrogen and $R^6$ is unsubstituted phenylmethyl;
22) when $R^2$ is —CO— and $R^3$ is NR$^5$R$^6$, $R^5$ is hydrogen and $R^6$ is unsubstituted phenyl;
23) when $R^2$ is —CO— and $R^3$ is NR$^5$R$^6$, $R^5$ is hydrogen and $R^6$ is 4-fluorophenyl;
24) when $R^2$ is —CO— and $R^3$ is NR$^5$R$^6$, $R^5$ is hydrogen and $R^6$ is $C_1$–$C_6$ alkyl;
25) when $R^2$ is —CO— and $R^3$ is NR$^5$R$^6$, $R^5$ is hydrogen and $R^6$ is selected from the group consisting of methyl, cyclohexyl, butyl, and isopropyl;

26) when $R^2$ is —CS— and $R^3$ is $NR^5R^6$, $R^5$ is hydrogen and $R^6$ is phenylmethyl;
27) when $R^2$ is —CS— and $R^3$ is $NR^5R^6$, $R^5$ is, hydrogen and $R^6$ is phenyl;
28) when $R^2$ is —CS— and $R^3$ is $NR^5R^6$, $R^5$ is hydrogen and $R^6$ is halo monosubstituted phenyl;
29) when $R^2$ is —CS— and $R^3$ is $NR^5R^6$, $R^5$ is hydrogen and $R^6$ is 4-fluorophenyl;
30) when $R^2$ is —CS— and $R^3$ is $NR^5R^6$, $R^5$ is hydrogen and $R^6$ is $C_1$–$C_6$ alkyl;
31) when $R^2$ is —CS— and $R^3$ is $NR^5R^6$, $R^5$ is hydrogen and $R^6$ is selected from the group consisting of methyl, butyl, and isopropyl;
32) $R^2$ is —CO— and $R^3$ is phenyl;
33) $R^2$ is —CO— and $R^3$ is phenylmethyl;
34) $R^2$ is —CO— and $R^3$ is $C_1$–$C_6$ alkyl;
35) $R^2$ is —CO— and $R^3$ is selected from the group consisting of methyl, butyl, cyclohexyl, and isopropyl;
36) $R^2$ is —CO— and $R^3$ is monosubstituted phenyl;
37) $R^2$ is —CO— and $R^3$ is selected from the group consisting of 2-nitrophenyl, 3-nitrophenyl, 3-cyanophenyl, 4-nitrophenyl, 4-cyanophenyl, 2-methylphenyl, 3-methylphenyl, 4-methylphenyl, 2-trifluoromethylphenyl, 3-trifluoromethylphenyl, 4-trifluoromethylphenyl, and 4-benzylphenyl;
38) 38)$R^2$ is —CO— and $R^3$ is substituted halophenyl;
39) $R^2$ is —CO— and $R^3$ is selected from the group consisting of 3,4,5,6-tetrafluorophenyl, 2-bromophenyl, 2-chlorophenyl, 2-fluorophenyl, 3-bromophenyl, 3-chlorophenyl, 2-iodophenyl, 3-fluorophenyl, 4-chlorophenyl, 4-iodophenyl, 4-bromophenyl, 2,3,4,5,6-pentafluorophenyl, 2,6-difluorophenyl, 2,5-difluorophenyl, 3,4-difluorophenyl, 2,3-difluorophenyl, 3,5-difluorophenyl, 2,3,5-trifluorophenyl, 2-methoxyphenyl, 3-methoxyphenyl, 4-methoxyphenyl, 2-hydroxyphenyl, and 4-hydroxyphenyl;
40) $R^2$ is —CO— and $R^3$ is 4-fluorophenyl;
41) $R^2$ is —CO— and $R^3$ is 4-fluorophenyl additionally monosubstituted;
42) $R^2$ is —CO— and $R^3$ is selected from the group consisting of 2-chloro-4-fluorophenyl, 2-iodo-fluorophenyl, 2,4-difluorophenyl, 3,4-difluorophenyl, 2-methyl-4-fluorophenyl;
43) $R^2$ is —CO— and $R^3$ is 4-fluorophenyl additionally disubstituted;
44) $R^2$ is —CO— and $R^3$ is selected form the group consisting of 2,4,6-trifluorophenyl, 3,4,5-trifluorophenyl, 2,3,4-trifluorophenyl, 2,4,5-trifluorophenyl;
45) $R^2$ is —CO— and $R^3$ is quinolinyl;
46) $R^2$ is —CO— and $R^3$ is trifluoromethoxy monosubstituted phenyl;
47) $R^2$ is —CO— and $R^3$ is $C_1$–$C_6$ alkoxy monosubstituted phenyl;
48) $R^2$ is —CO— and $R^3$ is hydroxy monosubstituted phenyl;
49) $R^2$ is —CO— and $R^3$ is $OR^5$;
50) when $R^2$ is —CO— and $R^3$ is $OR^5$; $R^5$ is phenyl;
51) when $R^2$ is —CO— and $R^3$ is $OR^5$; $R^5$ is phenylmethyl;
52) when $R^2$ is —CO— and $R^3$ is $OR^5$; $R^5$ is $C_1$–$C_6$ alkyl;
53) when $R^2$ is —CO— and $R^3$ is $OR^5$; $R^5$ is selected from the group consisting of methyl, butyl, and isopropyl;
54) when $R^2$ is —CO— and $R^3$ is $OR^5$; $R^5$ is $Ar^4$;
55) when $R^2$ is —CO— and $R^3$ is $OR^5$; $R^5$ is selected from thien-2-yl, pyridin-3-yl, pyridin-2-yl, and fur-2-yl;
56) the compound is an acid addition salt;
57) the compound is the hydrochloride salt;
58) the compound is the oxalate salt; and
59) the compound is the fumarate salt.

It will be understood that the above classes may be combined to form additional preferred classes.

It is preferred that the mammal to be treated by the administration of compounds of this invention is human.

The compounds of formula I wherein $R^1$ is $NH_2$ or $NR^2R^3$, and R, $R^2$ and $R^3$ are as defined above, may be prepared from substituted phenyl compounds of formula II and substituted compounds of formula III as illustrated in Scheme 1 below, where X is halide.

Scheme 1

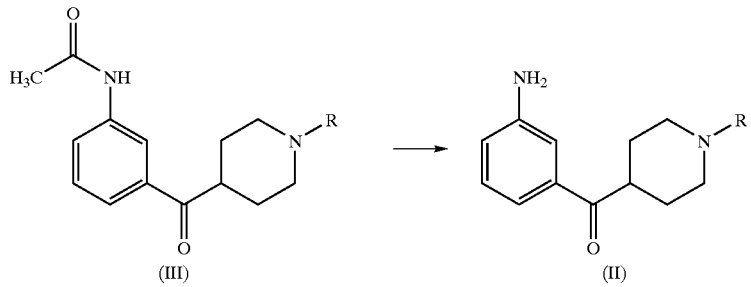

(III)　　　　　　　　　　(II)

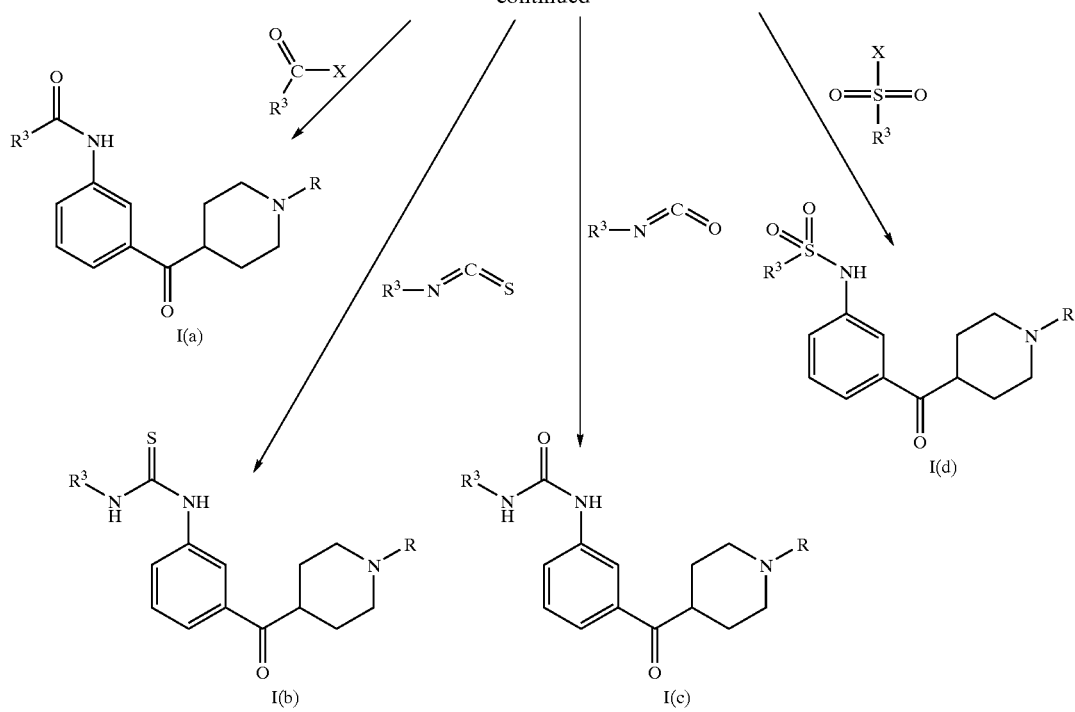

In general, the amide group of formula III may be hydrolyzed to an amine of formula II by well known methodology. See, e.g., Larock, "Comprehensive Organic Transformations," pgs. 431–436, VCH Publishers, New York, N.Y., 1989. Additionally, the amine of formula II can then be converted to the amide of formula I(a), the thiourea of formula I(b), the urea of formula I(c), or the sulfonamide of for formula I(d), by well known methodology. See, e.g., Siegal, *Tetrahedron Lett.*, 38:3357–3360, 1997. The acid halides, sulfonylhalides, isocyanates, and thioisocyanates of Scheme I are commercially available or may be prepared by methods known to those skilled in the art.

Additionally, a compound of formula II may be converted to a compound of the formula $NH—R^2—R^3$ by peptide coupling procedures, as those taught in the U.S. Pat. No. 5,708,008, herein incorporated by reference.

The compounds of formula III may be prepared from compounds of formula VI and compounds of formula V as illustrated in Scheme 2 below where R is as previously defined.

Scheme 2

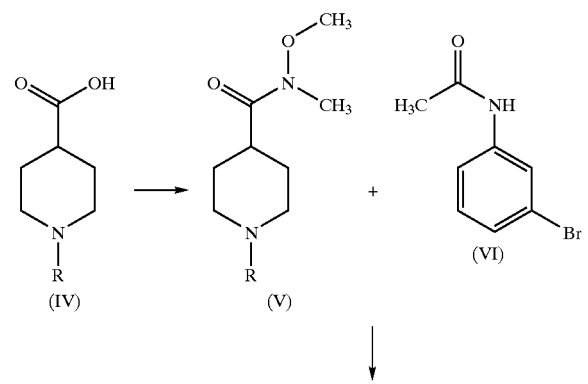

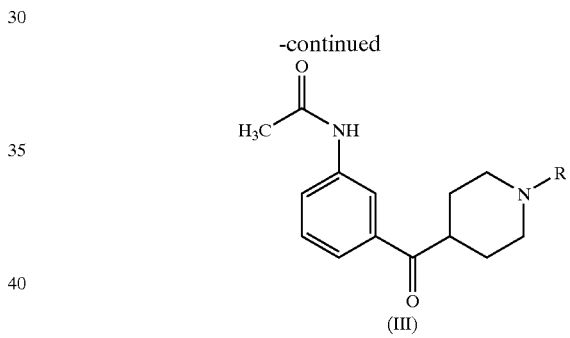

The N-methoxy-N-methylamide compounds of formula V are routinely prepared from commercially available N,O-dimethylhydroxylamine hydrochloride and the compound of formula IV or other activated derivative, by methods known to those skilled in the art. In a typical procedure, as outlined by Nahm, et. al., *Tetrahedron Lett.*, 22(39), pp. 3815–3818 (1981), 1 mmol of acid chloride and 1.1 mmol of N,O-dimethylhydroxylamine hydrochloride is dissolved in 10 mL of ethanol-free chloroform at about room temperature. The solution is cooled to about 0° C. and 2.2 mmol of pyridine is added. The mixture is partitioned between brine and a 1:1 mixture of ether and methylene chloride. The organic layer is dried with sodium sulfate and concentrated to afford the amide which is purified by silica gel chromatography or by distillation.

The 1-methylisonipecotic acid of formula IV can be prepared by methods well known in the art (*J. Med. Chem.* 36:457, 1993).

The compounds of formula III can be prepared by methods known to those skilled in the art. In a typical procedure, as outlined by Nahm et al., the compound of formula VI is reacted subsequentially with methyllithium then t-butyllithium, and is then added to a solution 1 mmol of N-methoxy-N-methylamide in 10 mL of dry THF at low temperature. The reaction mixture is stirred at the desired temperature until TLC shows the desired compound. The reaction is poured into 5% HCl in ethanol at about 0° C. and the mixture is partitioned between brine and a 1:1 mixture of ether and methylene chloride. The organic extract is dried with $Na_2SO_4$ and evaporated in vacuo. The product is then purified by chromatography if necessary or desired.

The compounds of formula I wherein $R^1$ is hydroxy or —$OSO_2Ar^2$, and $Ar^2$ is as defined above, may be prepared from substituted compounds of formula VII as illustrated in Scheme 3 below where R is as previously defined.

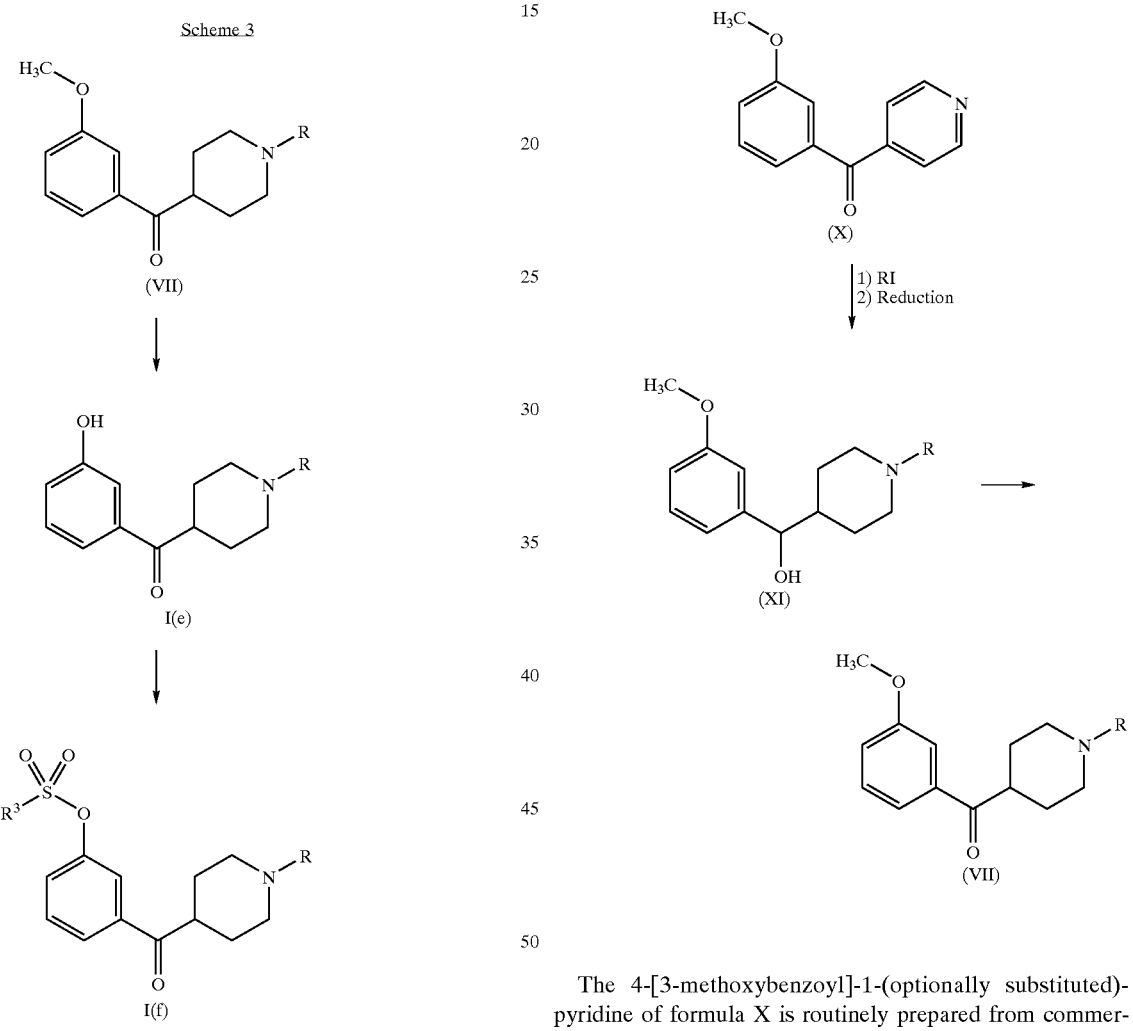

A compound of formula VII where $R^1$ is methoxy may be converted to a compound where $R^1$ is hydroxy by cleaving the ether by methods well known to one of ordinary skill in the art, such as that generally described in Bhatt and Kulkarni, *Synthesis*, 249–282 (1983).

A compound of formula I(e) where $R^1$ is hydroxy may be converted to a compound of the formula —$OSO_2Ar^2$ by methods well known to one of ordinary skill in the art, such as that taught by March, *Advanced Organic Chemisry*, 3rd ed., pg. 44, 1985.

The compounds of formula VII may be prepared from compounds of formula VIII and formula IX as illustrated in Scheme 4 below where R is as previously defined.

The 4-[3-methoxybenzoyl]-1-(optionally substituted)-pyridine of formula X is routinely prepared from commercially available 3-bromoanisole and ethyl isonicotinate (*Journal of Org. Chem.* 52:5026, 1987).

A compound of formula X may be converted to a quaternary salt then reduced by methods well known in the art to form a compound of formula XI. The alcohol of formula XI may be converted to the ketone of formula VII by methods well known to the skilled artisan, such as that generally taught by *Journal of Org. Chem.* 51:5472, 1986.

A preferred process for preparation of the compounds of formula I(a):

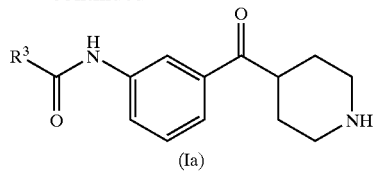

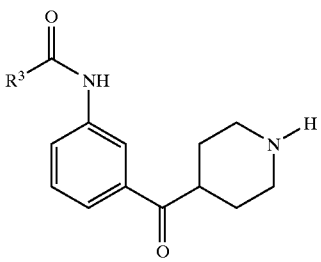

wherein R[3] is hydrogen, optionally substituted $C_1$–$C_6$ alkyl, Ar[3], —NR[5]R[6], or OR[5];

R[5] and R[6] are independently hydrogen, optionally substituted $C_1$–$C_8$ alkyl, or Ar[4]; or R[6] and R[5] combine, together with the nitrogen atom to which they are attached, to form a pyrrolidine, piperidine, piperazine, 4-substituted piperazine, morpholine or thiomorpholine ring; and Ar[3] and Ar[4] are independently an optionally substituted phenyl or optionally substituted heteroaryl, is illustrated in Scheme 5 below.

Scheme 5

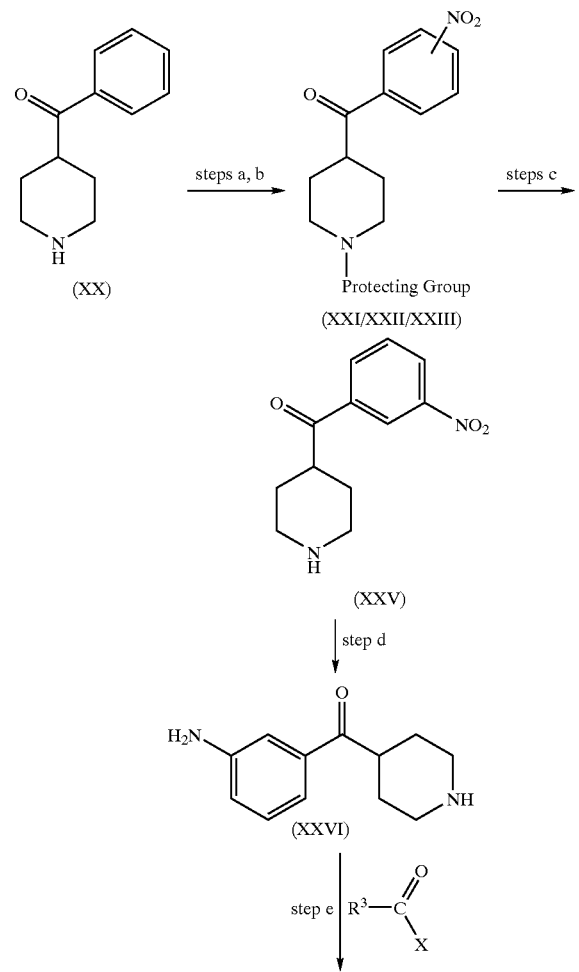

The process of this invention is performed by the following steps:

(a) protecting 4-benzoylpiperidine hydrochloride to form N-protected 4-benzoylpiperidine hydrochloride;

(b) nitrating the N-protected 4-benzoylpiperidine hydrochloride to form a mixture of N-protected 4-(mononitrobenzoyl)piperidines;

(c) deprotecting the N-protected 4-(mononitrobenzoyl) piperidine mixture to form a mixture of 4-(mononitrobenzoyl)piperidines;

(d) separating 4-(3-nitrobenzoyl)piperidine from the mixture of 4-(mononitrobenzoyl)piperidines;

(e) reducing 4-(3-nitrobenzoyl)piperidine to form 4-(3-aminobenzoyl)piperidine; and (f) acylating the 4-(3-aminobenzoyl)piperidine.

4-[3-(substituted)benzoyl]piperidine HCl of formula I(a) is prepared in one pot.

Step a) of the process of the invention is performed by combining the 4-benzoylpiperidine hydrochloride with a source useful for applying an amino protecting group in an appropriate medium. Once the reaction is complete, the resulting N-protected 4-benzoylpiperidine can be isolated by standard extractions and filtrations. If desired, the N-protected 4 benzoylpiperidine may be further purified by chromatography or crystallization as appropriate.

The substrate may first be dissolved in an appropriate reaction medium and then added to a mixture of the source of the protecting group. Also, a solution of the substrate in an appropriate reaction medium may be added to a slurry of the source of the protecting group in the same reaction medium. Preferably, the source of the protecting group may act as the reaction media.

Reaction media useful for step a) of the invention must be capable of dissolving a sufficient amount of the 4-benzoylpiperidine and the protecting group for the reaction to proceed. Organic solvents useful as reaction media for the process of this invention include $CHCl_3$, $CH_2Cl_2$, hexane, cyclohexane, nitromethane, nitrobenzene, acetonitrile, ether, THF, dioxane, trichloroacetic anhydride, dichloroacetic anhydride, and preferably trifluoroacetic anhydride. The skilled artisan will appreciate that the anhydrides named above will serve to protect the amino group as well as act as reaction solvent.

Source of the protecting group useful for the process of step a) of the invention includes acid halides, sulfenyl halides, sulfonyl halides, chloroformates, acid anhydrides, and preferably trifluoroacetic anhydride, which may also act as the reaction medium.

The process of step a) may be carried out over a large range of concentrations, from about 0.5 molar to about 5 molar of the protecting group. The reaction may also be performed on slurries of the protecting group so long as a sufficient amount of the protecting group is soluble in the reaction medium for the reaction to proceed. Preferably the process is performed in an excess of the source of the protecting group acting as the reaction medium.

Reactions of step a) may be performed between about 5° C. and about 40° C., preferably between about 10° C. and about 25° C. The skilled artisan will appreciate that the reaction rates will decrease as temperatures are lowered and increase as temperatures are elevated.

After treatment with the source of the protecting group, the N-protected 4-benzoylpiperidine is treated with the source of nitronium ion to form a mixture of N-protected 4-(mononitrobenzoyl)piperidines. The N-protected 4-benzoylpiperidine may first be dissolved in an appropriate reaction medium and then added to a mixture of the source of the nitronium ion. Also, a solution of the N-protected 4-benzoylpiperidine in an appropriate reaction medium may be added to a slurry of the source of the nitronium ion in the same reaction medium.

Reaction media useful for step b) of the process of the invention must be capable of dissolving a sufficient amount of the 4-benzoylpiperidine, the source of the nitronium ion, and the protecting group for the reaction to proceed. Organic solvents useful as reaction media for the process of this invention include $CHCl_3$, $CH_2Cl_2$, hexane, cyclohexane, nitromethane, nitrobenzene, acetonitrile, ether, THF, dioxane, trichloroacetic anhydride, dichloroacetic anhydride, and preferably trifluoroacetic anhydride.

Source of the nitronium ion useful for the process of step b) of the invention include fuming nitric acid and inorganic nitrate salts, preferably ammonium nitrate.

Step b) may be carried out over a large range of concentrations, from about 0.5 molar to about 2 molar of the source of nitronium ion. The reaction may also be performed on slurries of the source of nitronium ion so long as a sufficient amount of the nitronium ion is soluble in the reaction medium for the reaction to proceed. Preferably the process is performed at a concentration from about 1 molar to about 2 molar. A concentration of about 0.9 molar to about 1.4 molar is most preferred.

Reactions of step b) may be performed between about 5° C. and about 40° C., preferably between about 10° C. and about 25° C. The skilled artisan will appreciate that the reaction rates will decrease as temperatures are lowered and increase as temperatures are elevated.

Preferably steps a) and b) are combined and the source of the protecting group is acting as reaction medium, in which the source of the nitronium ion may be added directly to the reaction media slurry. All of these methods are useful for the process of the present invention. Step c) of the process of the invention is performed by combining the N-protected 4-(mononitrobenzoyl)-piperidine product of step b) with an appropriate deprotecting agent in a suitable reaction medium. The skilled artisan will appreciate that the nature of the deprotecting agent will depend upon the specific protecting group employed. For example, a strong acid or base will remove a trifluoroacetate protecting group. However, hydrochloric acid is preferred. Once the reaction is complete, as measured by consumption of the substrate, the resulting 4-(mononitrobenzoyl)piperidine products are isolated by standard extractions and filtrations. If desired, the 4-(mononitrobenzoyl)piperidine products may be further purified by chromatography or crystallization as appropriate.

The order and manner of combining the reactants are not important and may be varied as a matter of convenience. The N-protected 4-(mononitrobenzoyl)piperidine products and deprotecting compound may first be combined and then the reaction medium added. Alternatively, the substrate may first be dissolved in an appropriate reaction medium and this solution added to a mixture of the deprotecting compound. Also, a solution of the substrate in an appropriate reaction medium may be added to a slurry of the deprotecting compound in the same reaction medium. Furthermore, a first slurry containing part of the reactants in an appropriate reaction medium may be added to a second slurry of the remaining reactants in an appropriate reaction medium as is desired or convenient. All of these methods are useful for the process of the present invention.

Reaction media useful for step c) of the invention must be capable of dissolving a sufficient amount of the N-protected 4-(mononitrobenzoyl)piperidine products for the reaction to proceed. Organic solvents useful as reaction media for the process of this invention depend upon the choice of deprotecting agent and may include water, DMF, THF, acetone, MeOH, EtOH or isopropyl alcohol.

Depending upon the choice of deprotecting agent, reactions of step c) may be performed between about 40° C. and about 100° C. The skilled artisan will appreciate that the reaction rates will decrease as temperatures are lowered and increase as temperatures are elevated.

Step c) may be carried out over a large range of id concentrations, from about 0.05 molar to about 1 molar of the N-protected 4-(mononitrobenzoyl)-piperidine products, dependent upon the solubility of the particular product in the chosen reaction medium. Preferably the process is performed at a concentration from about 0.05 molar to about 0.2 molar. A concentration of about 0.08 molar to about 0.1 molar is most preferred.

Step e) of the process of the invention is performed by treating the 4-(mononitrobenzoyl)piperidine product with an appropriate reducing agent in a suitable reaction medium. Once the reaction is complete, as measured by consumption of the substrate, the resulting 4-(monoaminobenzoyl) piperidine products are isolated by standard extractions and filtrations. If desired, the 4-(monoaminobenzoyl)piperidine products may be further purified by chromatography or crystallization as appropriate.

The order and manner of combining the reactants are not important and may be varied as a matter of convenience. The 4-(mononitrobenzoyl)piperidine products and the reducing agent may first be combined and then the reaction medium added. Alternatively, the substrate may first be dissolved in an appropriate reaction medium and this solution added to a mixture of the reducing agent. Also, a solution of the substrate in an appropriate reaction medium may be added to a slurry of the reducing agent in the same reaction medium. Furthermore, a first slurry containing part of the reactants in an appropriate reaction medium may be added to a second slurry of the remaining reactants in an appropriate reaction medium as is desired or convenient. All of these methods are useful for the process of the present invention.

Compounds useful as reducing agents include $PtO_2$ and preferably Pd/C.

Reaction media useful for step e) must be capable of dissolving a sufficient amount of the 4-(mononitrobenzoyl) piperidine products for the reaction to proceed. Organic solvents useful as reaction media for the process of this invention depend upon the choice of reducing agent and may include water, DMF, isopropanol, ethanol or methanol.

The control of temperature is critical during hydrogenation. Depending upon the choice of reducing agent, reactions of step e) may be performed above 20° C., preferably above 30° C. The skilled artisan will appreciate that contamination of the 4-(monoaminobenzoyl)piperidine HCl compounds with by-products may result at lower temperatures.

Step e) may be carried out over a large range of concentrations, from about 0.05 molar to about 1 molar of the 4-(mononitrobenzoyl)piperidine products, dependent upon the solubility of the particular product in the chosen reaction medium. Preferably the process is performed at a concentration from about 0.1 molar to about 0.5 molar. A concentration of about 0.2 molar to about 0.3 molar is most preferred.

Step f) of the invention is performed by treating the 4-(monoaminobenzoyl)piperidine product of step e) with an appropriate acylating agent in a suitable reaction medium. Once the reaction is complete, as measured by consumption of the substrate, the resulting 4-((substituted)benzoyl) piperidine products are isolated by standard extractions and filtrations. If desired, the 4-((substituted)benzoyl)piperidine products may be further purified by chromatography or crystallization as appropriate.

The order and manner of combining the reactants are not important and may be varied as a matter of convenience. The 4-(monoaminobenzoyl)piperidine products and the acylating agent may first be combined and then the reaction medium added. Alternatively, the substrate may first be dissolved in an appropriate reaction medium and this solution added to a mixture of the acylating agent. Also, a solution of the substrate in an appropriate reaction medium may be added to a slurry of the acylating agent in the same reaction medium. Furthermore, a first slurry containing part of the reactants in an appropriate reaction medium may be added to a second slurry of the remaining reactants in an appropriate reaction medium as is desired or convenient. All of these methods are useful for the process of the present invention.

Compounds useful as acylating agents include acid anhydrides, and preferably acid halides. A more preferred acylating agent is the acid chloride.

The use of propylene oxide as the reaction medium during the acylation of the 4-(monoaminobenzoyl)piperidine HCl is essential.

Depending upon the choice of acylating agent, reactions of step f) may be performed between about 0 and about 40° C. The skilled artisan will appreciate that the reaction rates will decrease as temperatures are lowered and increase as temperatures are elevated.

Step f) may be carried out over a large range of concentrations, from about 0.1 molar to about 1 molar of the 4-(monoaminobenzoyl)piperidine products, dependent upon the solubility of the particular product in the chosen reaction medium. Preferably the process is performed at a concentration from about 0.1 molar to about 0.5 molar. A concentration of about 0.1 molar to about 0.2 molar is most preferred.

The skilled artisan will appreciate that the mixture of isomers resulting from the nitration described in step b) of the process of the present invention may be separated at any point convenient or desired. A preferred embodiment of this invention is that the desired 4-(3-nitrobenzoyl)piperidine product is isolated as step d) of the process of the invention. That is, after deprotection, but prior to reduction of the nitro group to provide the corresponding amine. The 4-(3-nitrobenzoyl)piperidine may be isolated from the mixture by standard chromatographic techniques or crystallographic techniques.

The following Preparations and Examples are provided to better elucidate the practice of the present invention and should not be interpreted in any way as to limit the scope of same. Those skilled in the art will recognize that various modifications may be made while not departing from the spirit and scope of the invention.

Preparations

Preparation 1

1-methylisonipecotic Acid

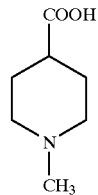

Isonipecotic acid (50 g, 0.387 mole) was dissolved in water (500 ml) and 37% formaldehyde (125 ml). 10% Palladium on carbon (50 g) was added and the mixture was shaken under a hydrogen atmosphere at 60 psi at room temperature for 18 hours.

The catalyst was filtered, washed with water, and the filtrate was concentrated under reduced pressure. The residue was slurried in water and concentrated in vacuo. The residue was slurried in ethanol and concentrated in vacuo to give a white solid. Drying under vacuum at ambient temperature for 18 h gave 42.2 g (76%) of a white solid, mp 173–5° C. MS(m/e): 143 (M$^+$).

Analysis for $C_7H_{13}NO_2$:

Calcd: C, 58.72; H, 9.15; N, 9.78; Found: C, 58.24; H, 9.59; N. 9.71.

Preparation 2

N-methoxy-N-methyl(1-methylisonipecotamide)

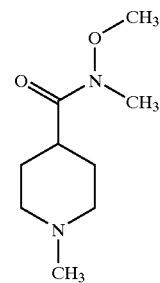

1-Methylisonipecotic acid (5.5 g, 38.4 mmol) was dissolved in dimethylformamide (100 ml) with heating. Diisopropylethylamine (8.0 ml, 46.1 mmol), 1-hydroxybenzotriazole (5.2 g, 38.4 mmol), and N,O-dimethylhydroxylamine hydrochloride (4.1 g, 42.2 mmol) were added and the reaction mixture was stirred 5 min. 1-(3-dimethylaminopropyl)-3-ethylcarbodiimide hydrochloride (7.4 g, 38.4 mmol) was added and the resulting homogeneous solution was stirred for 63 hours at ambient temperature. The solvent was removed under reduced pressure. The residue was dissolved in water and the solution was basified to pH 9 with 5N sodium hydroxide solution. This aqueous solution was extracted with methylene chloride then saturated with sodium chloride and extracted with chloroform/isopropanol (3/1). The combined organic extracts were dried over sodium sulfate and the solvent was removed under reduced pressure to give 9.5 g of a yellow liquid. Purification by flash chromatography (silica gel, methylene chloride:methanol:ammonium hydroxide, 100:10:1) gave 5.7 g (80%) of product as a light yellow liquid.

MS (m/e): 186(M$^+$).

Analysis for $C_9H_{18}N_2O_2$:

Preparation 3

3-bromoacetanilide

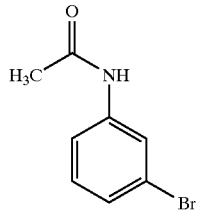

A solution of acetyl chloride (44.0 ml, 0.619 mol) in tetrahydrofuran (20 ml) was added dropwise to a 0° C. solution of 3-bromoaniline (101.5 g, 0.590 mol) and triethylamine (87.4 ml, 0.625 mol) in tetrahydrofuran (550 ml). The resulting mixture was stirred 16 h at room temperature. The reaction mixture was quenched with ice/water (500 ml), acidified to pH 1 with 5N hydrochloric acid, and extracted with ethyl acetate. The ethyl acetate extracts were washed with 1N hydrochloric acid, water, brine, then dried over sodium sulfate. The solvent was removed under reduced pressure to give 125.5 g of a red solid. Recrystallization from ethyl acetate/hexanes gave 69.2 g of an off white powder. Filtered a second crop of product to give 26 g of a tan powder. Total yield=75%.

MS(m/e): 214(M$^+$).

Analysis for $C_8H_8BrNO$:

Calcd: C, 44.89; H, 3.77; N, 6.54; Found: C, 45.10; H, 3.78; N, 6.57.

Preparation 4

4-fluoro-2-iodobenzoic acid

To a 0° C. mixture of 2-amino-4-fluorobenzoic acid (1.18 g, 7.6 mmol) in 12N hydrochloric acid (2.3 mL) and water (13.7 mL) was added dropwise a solution of sodium nitrite (543 mg, 7.9 mmol) in water (1.2 mL). This resulting diazonium salt solution was stirred 10 min at 0° C. A solution of potassium iodide (1.9 g) in sulfuric acid (450 35 μL) and water (3.2 mL) was added dropwise to the 0° C. solution. The reaction mixture was heated to 100° C. for 2 h then cooled to room temperature. 10% sodium bisulfite solution was added and stirred. The precipitate was filtered, washed with water, air dried and recrystallized from toluene.

mp 144–6° C. MS(m/e): 265(M-1).

Analysis for $C_7H_4FIO_2$:

Calcd: C, 31.61; H, 1.52, N, 0; I, 47.71; Found: C, 31.93; H, 2.14; N, 0.14; I, 42.75.

Preparation 5

4-[3-methoxybenzoyl]pyridine

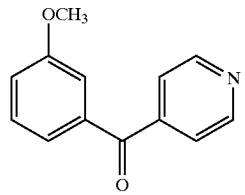

n-Butyllithium (4.9 ml, 7.9 mmol, 1.6 M in hexanes) was added dropwise to a -73° C. solution of 3-bromoanisole (1.48 g, 7.9 mmol) in tetrahydrofuran (30 ml). The reaction mixture was stirred 25 min at -73° C. A solution of ethyl isonicotinate (1.3 g, 8.7 mmol) in tetrahydrofuran (20 ml) was added dropwise. The reaction mixture was stirred 1.5 h at -73° C. then was allowed to room temperature over 15 min. The reaction mixture was quenched with water/brine and extracted with diethyl ether. The organic extracts were washed with brine, dried over sodium sulfate and concentrated in vacuo to give 1.8 g of a yellow solid. Purification by radial chromatography (silica gel, 6000 micron rotor, 2% methanol/methylene chloride) then again by radial chromatography (silica gel, 4000 micron rotor, 1% methanol/methylene chloride) gave 1.2 g of a mixture of product and ethyl isonicotinate. This mixture was dissolved ethanol (7 mL) and 5N sodium hydroxide (7 mL) and stirred at room temperature for 16 h. The solvent was removed under reduced pressure. The residue was diluted with water and extracted with methylene chloride. The methylene chloride extracts were washed with 1N sodium hydroxide, brine, dried over sodium sulfate and concentrated in vacuo to 860 mg of an orange oil. MS(m/e): 213(M$^+$).

Analysis for $C_{13}H_{11}NO_2$:

Calcd: C, 73.23; H, 5.20; N, 6.59; Found: C, 73.38; H, 5.34; N, 6.47.

Preparation 6

4-[3-methoxybenzoyl]-1-methylpyridinium iodide

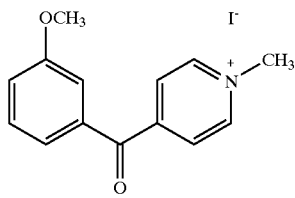

A mixture of 4-[3-methoxybenzoyl]pyridine(790 mg, 3.7 mmol) and iodomethane (1.15 ml, 18.5 mmol) in acetone (10 mL) was stirred at room temperature for 48 h. The precipitate was filtered, washed with diethyl ether and dried in vacuo to give 1.2 g (91%) of an orange powder.

Mp 173–174° C. MS(m/e): 228 (M$^+$).

Analysis for $C_{14}H_{14}INO_2$:

Calcd: C, 47.34; H, 3.97; N, 3.94; Found: C, 47.91; H, 3.81; N, 3.87.

Preparation 7

[(3-methoxyphenyl)(1-methyl(piperid-4-yl)]methanol

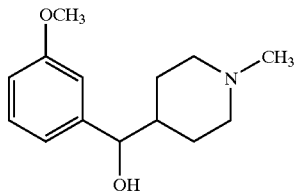

A mixture of 4-[3-methoxybenzoyl]-1-methylpyridine iodide (730 mg, 2.1 mmol) and platinum oxide (100 mg, 0.44 mmol) in methanol was stirred under a hydrogen atmosphere for 2 h. The catalyst was filtered and washed with methanol then water. The filtrate was concentrated under reduced pressure. The resulting residue was dissolved in methylene chloride, washed with 1N sodium hydroxide, dried over sodium sulfate and concentrated in vacuo to give 490 mg of a clear colorless oil. Purification by radial chromatography (silica gel, 2000 micron rotor, methylene chloride:methanol:ammonium hydroxide, 100:10:1) gave 425 mg (87%) of a white solid. Mp 102–104° C. MS(m/e): 235($M^+$).

Analysis for $C_{14}H_{21}NO_2$:

Calcd: C, 71.46; H, 9.00; N, 5.95; Found: C, 71.39; H, 8.94; N, 6.17.

Preparation 8

4-[3-methoxybenzoyl]-1-methylpiperidine oxalate

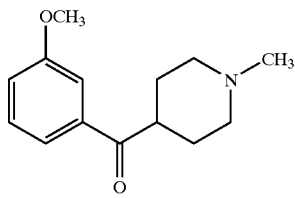

A mixture of [(3-methoxyphenyl)(1-methyl(piperid-4-yl)]methan-1-ol (195 mg, 0.83 mmol) and pyridinium dichromate (468 mg, 1.2 mmol) in methylene chloride was stirred at room temperature for 1 h. The reaction mixture was quenched with isopropanol (5 mL) and stirred for 15 min. This reaction mixture was combined with an identical reaction that used 0.11 mmol of [(3-methoxyphenyl)(1-methyl(piperid-4-yl)]methanol. The mixture was filtered through filter agent, washed with methylene chloride and isopropanol. The filtrate was concentrated under reduced pressure. The product was dissolved then filtered through silica gel using methylene chloride:methanol:ammonium hydroxide (100:10:1) as the solvent. The filtrate was concentrated under reduced pressure to give 200 mg of a brown residue. Purification by radial chromatography (silica gel, 2000 micron rotor, methylene chloride:methanol:ammonium hydroxide, 100:5:0.5) gave 160 mg (83%) of a brown oil. Crystallized as the oxalic acid salt from ethyl acetate/methanol.

Mp 155–6.5° C. MS(m/e): 233($M^+$).

Analysis for $C_{16}H_{21}NO_6$:

Calcd: C, 59.43; H, 6.55; N, 4.33; Found: C, 59.51; H, 6.46; N, 4.30.

Preparation 9

4-[3-hydroxybenzoyl]-1-methylpiperidine

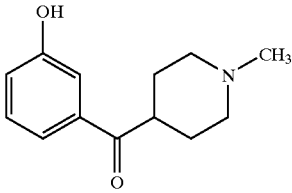

A solution of 4-[3-methoxybenzoyl]-1-methylpiperidine (260 mg, 1.1 mmol) in 48% hydrobromic acid (10 mL) was refluxed for 1 h. The reaction mixture was concentrated under reduced pressure to a brown oil. The oil was dissolved in water, basified to pH 9 with ammonium hydroxide, and extracted with methylene chloride. Sodium chloride was added to the aqueous phase and extracted with chloroform/isopropanol (3:1). The organic extracts were combined, dried over sodium sulfate, and concentrated in vacuo to give 240 mg of a tan solid. Purification by radial chromatography (silica gel, 2000 micron rotor, methylene chloride:methanol:ammonium hydroxide, 100:10:1) gave 214 mg (88%) of a tan crystalline solid. Mp 161–4° C. MS(m/e): 220(M+1).

Analysis for $C_{13}H_{17}NO_2$:

Calcd: C, 71.21; H, 7.81; N, 6.39; Found: C, 70.96; H, 7.51; N, 6.31.

Preparation 10

4-[2-(formamidyl)-5-(4-fluorobenzamidyl)benzoyl]-1-methylpiperidine

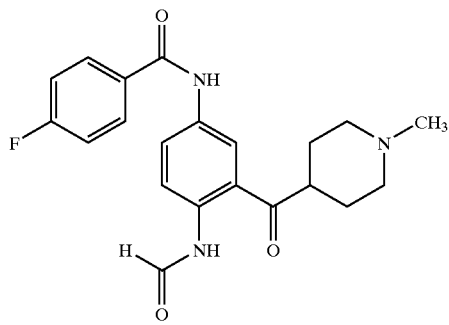

A solution of sodium metaperiodate (2.43 g, 11.3 mmol) in water (20 ml) was added dropwise to a solution of 5-(4-fluorobenzamidyl-3-(1-methylpiperidin-4-yl)-1H-indole hydrochloride (2.0 g, 5.2 mmol) in methanol (70 ml) and water (70 ml). Methanol (20 ml) and water (20 ml) were added to aid in stirring. The reaction mixture was stirred at room temperature for 48 hours. The precipitate was filtered and discarded. The filtrate was diluted with 10% aqueous sodium bicarbonate solution (300 ml) and extracted with ethyl acetate. The organic extracts were washed with water and brine, dried over sodium sulfate, filtered and concentrated in vacuo to give 1.9 g of a dark foam. Purification by flash chromatography (silica gel, methylene chloride:methanol:ammonium hydroxide, 100:5:0.5 then 100:7.5:0.5) gave 1.0 g (50.5%) of the title compound as a white solid. MS(m/e): 383 ($M^+$).

EXAMPLES

Example 1

4-[3-(methylamidyl)benzoyl]-1-methylpiperidine

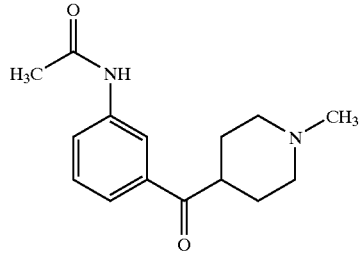

Methyllithium (1.4 M in diethyl ether, 37.4 ml, 52.3 mmol) was added to a −78° C. solution of 3-bromoacetanilide (11.5 g, 53.7 mmol) in tetrahydrofuran (250 ml). The reaction was stirred 15 min at −78° C. Tert-butyllithium (1.7 M in pentane, 62.4 ml, 106 mmol) was added over 30 min to the −78° C. reaction mixture. The reaction was stirred 10 min at −78° C. N-methoxy-N-methyl (1-methyl(4-piperidyl))formamide (5.0 g, 26.8 mmol) in tetrahydrofuran (20 ml) was added dropwise to give a homogeneous yellow solution. The reaction mixture was stirred and allowed to warm to room temperature over 21 hours. The reaction mixture was cooled to 10° C., quenched with ice, and extracted with 1N hydrochloric acid solution. The aqueous extracts were washed with diethyl ether, basified to pH 12 with 5N sodium hydroxide solution and extracted with diethyl ether. The diethyl ether extracts were dried over sodium sulfate and the solvent was removed under reduced pressure to give 6.1 g of a yellow oil. The basic aqueous solution was again extracted with chloroform/isopropanol (3:1). These extracts were dried over sodium sulfate and the solvent was removed under reduced pressure to give 3.4 g of a yellow oil. Both oils were combined and purified by flash chromatography (silica gel, methylene chloride:methanol:ammonium hydroxide, 100:7.5:0.75) to yield 5.7 g (81%) of product as a yellow oil.

MS(m/e): 261(M+1), 259(M−1).

Example 2

4-[3-(methylamidyl)benzoyl]-1-methylpiperidine oxalate

4-[3-(methylamidyl)benzoyl]-1-methylpiperidine (283 mg, 1.1 mmol) in ethyl acetate was added to oxalic acid (99 mg, 1.1 mmol) in ethyl acetate. The resulting precipitate was filtered, washed with ethyl acetate, and dried under vacuum to give 270 mg (71%) of tan powder.

mp 153–4° C. MS(m/e): 261(M+1), 259(M−1).

Analysis for $C_{17}H_{22}N_2O_6$:

Calcd: C, 58.28; H, 6.33; N, 8.00; Found: C, 58.03; H, 6.56; N, 7.74.

Example 3

4-[3-aminobenzoyl]-1-methylpiperidine

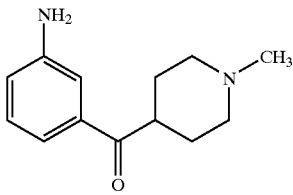

A solution of 4-[3-(methylamidyl)benzoyl]-1-methylpiperidine (5.68 g, 21.8 mmol) in 6N hydrochloric acid (140 ml) was heated to reflux for 1.75 hours. The solvent was removed under reduced pressure. The residue was dissolved in water (25 ml) and basified with concentrated ammonium hydroxide. The resulting precipitate and solution were chilled for 1 h, filtered, and dried under vacuum at room temperature for 16 h to give 3.6 g of a tan powder (76%).

MS(m/e): 219(M+1).

Analysis for $C_{13}H_{18}N_2O$:

Calcd: C, 71.53; H, 8.31; N, 12.83; Found: C, 71.52; H, 8.20; N, 12.90.

Example 4

4-[3-(4-fluorobenzamidyl)benzoyl]-1-methylpiperidine

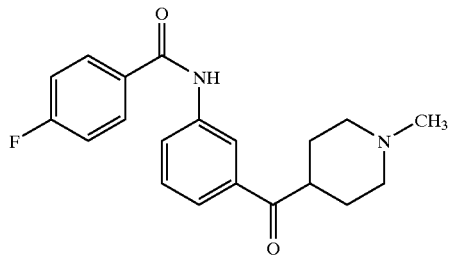

4-Fluorobenzoyl chloride (0.98 ml, 8.3 mmol) was added dropwise to a 0° C. solution of 4-[3-aminobenzoyl]-1-methylpiperidine (1.64 g, 7.5 mmol) and triethylamine (1.3 ml, 9.0 mmol) in tetrahydrofuran (20 ml). The reaction mixture stirred 2 h at room temperature, diluted with ethyl acetate and 1N sodium hydroxide solution and extracted with ethyl acetate. The ethyl acetate extracts were washed with water, brine, then dried over sodium sulfate. Solvent was removed under reduced pressure to give 2.5 g (98%) of a foam.

MS(m/e): 341(M+1), 339(M−1).

Example 5

4-[3-(4-fluorobenzamidyl)benzoyl]-1-methylpiperidine oxalate hemihydrate

A solution of 4-[3-(4-fluorobenzamidyl)benzoyl]-1-methylpiperidine (200 mg, 0.59 mmol) in ethyl acetate was added to a solution of oxalic acid (53 mg, 0.59 mmol) in ethyl acetate. The resulting precipitate was filtered, washed with ethyl acetate, and dried at room temperature under vacuum. Obtained 250 mg (99%) of the oxalate salt as a tan powder.

mp—foams at 95° C.

MS(m/e): 341(M+1).

Analysis for $C_{22}H_{23}FN_2O_6 \cdot 0.5H_2O$:

Calcd: C, 60.13; H, 5.50; N, 6.37; Found: C, 59.94; H, 5.44; N, 6.48.

Example 6

4-[3-(fur-2-ylamidyl)benzoyl]-1-methylpiperidine hydrochloride

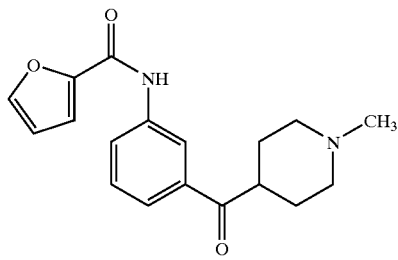

2-Furoyl chloride (0.15 ml, 1.5 mmol) was added to a solution of 4-[3-aminobenzoyl]-1-methylpiperidine (257 mg, 1.2 mmol) and triethylamine (0.2 ml, 1.4 mmol) in tetrahydrofuran (10 ml). The reaction mixture was stirred 2 h at room temperature. The reaction mixture was diluted with ethyl acetate and 1N sodium hydroxide then extracted with ethyl acetate. The ethyl acetate extracts were washed with 1N sodium hydroxide, water, brine, then dried over sodium sulfate. The solvent was removed under reduced pressure to give 440 mg. Purification by radial chromatography (silica gel, 2000 micron rotor, methylene chloride:methanol:ammonium hydroxide, 100:5:0.5) gave 350 mg (95%) of a foam. Crystallization as the hydrochloric acid salt from ethyl acetate/ethanol provided 320 mg of a yellow powder with mp>200° C. MS(m/e): 313(M+1), 311(M−1).

Analysis for $C_{18}H_{21}ClN_2O_3$:

Calcd: C, 61.98; H, 6.07; N, 8.03; Found: C, 61.86; H, 5.78; N, 8.02.

Example 7

4-[3-(benzamidyl)benzoyl]-1-methylpiperidine oxalate

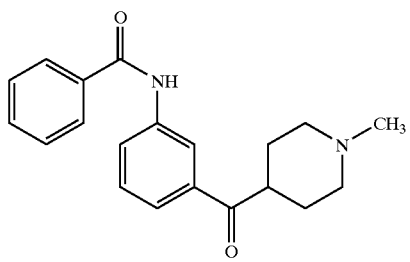

Benzoyl chloride (0.12 ml, 1.0 mmol) was added to a solution of 4-[3-aminobenzoyl]-1-methylpiperidine (200 mg, 0.92 mmol) and triethylamine (0.15 ml, 1.1 mmol) in tetrahydrofuran (10 ml). The reaction mixture was stirred 64 h at room temperature. The reaction mixture was diluted with ethyl acetate and 1N sodium hydroxide solution then extracted with ethyl acetate. The ethyl acetate extracts were washed with 1N sodium hydroxide solution, water, brine, then dried over sodium sulfate. The solvent was removed under reduced pressure to give 324 mg of a yellow oil. Purification by radial chromatography (silica gel, 2000 micron rotor, methylene chloride:methanol:ammonium hydroxide, 100:5:0.5) gave 287 mg (97%) of a yellow oil. Crystallization as the oxalic acid salt from ethyl acetate provided 240 mg of yellow crystals. MS(m/e): 323(M+1), 321(M−1).

Analysis for $C_{22}H_{24}N_2O_6$:

Calcd: C, 64.07; H, 5.86; N, 6.79; Found: C, 63.89; H, 5.94; N, 7.07.

Example 8

4-[3-(methylsulfonamino)benzoyl]-1-methylpiperidine

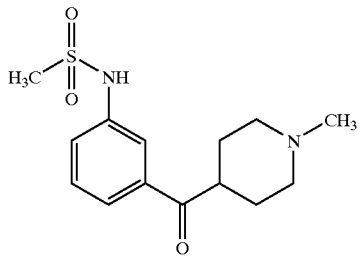

Methanesulfonyl chloride (0.2 ml, 2.6 mmol) was added to a mixture of 4-[3-aminobenzoyl]-1-methylpiperidine dihydrochloride (526 mg, 1.8 mmol) and triethylamine (0.8 ml, 5.8 mmol) in DMF (17 ml). The reaction mixture was stirred 16 h at room temperature then concentrated in vacuo. Purification by flash chromatography (silica gel, methylene chloride:methanol:ammonium hydroxide, 100:10:1) then radial chromatography (silica gel, 2000 micron rotor, methylene chloride:methanol, 97.5:2.5 then methylene chloride:methanol:ammonium hydroxide, 100:5:1) gave 57 mg (11%) of product. MS (m/e): 296(M+).

Analysis for $C_{14}H_{20}N_2O_3S$:

Calcd: C, 56.74; H, 6.80; N, 9.45; Found: C, 56.94; H, 6.68; N, 9.22.

Example 9

4-[3-((pyrid-4-yl)amidyl)benzoyl]-1-methylpiperidine dihydrochloride

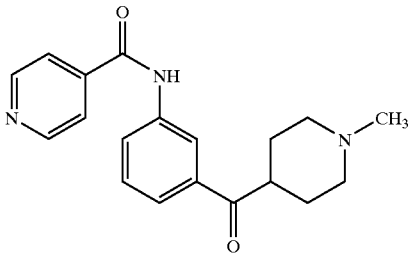

4-[3-aminobenzoyl]-1-methylpiperidine (200 mg, 0.92 mmol) and dimethylformamide (5 ml) were added in one portion to a solution of isonicotinic acid (124 mg, 1.0 mmol), 1-hydroxybenzotriazole (136 mg, 1.0 mmol), 1-(3-dimethylaminopropyl)-3-ethylcarbodiimide hydrochloride (193 mg, 1.0 mmol) in dimethylformamide (5 ml). The reaction mixture was stirred 24 h at room temperature. The reaction mixture was diluted with ethyl acetate and 10% potassium carbonate solution then extracted with ethyl acetate. The ethyl acetate extracts were washed with water, brine, then dried over sodium sulfate. The solvent was removed under reduced pressure to give 460 mg. Purification by radial chromatography (silica gel, 2000 micron rotor, methylene chloride:methanol:ammonium hydroxide, 100:5:0.5) then again by radial chromatography (silica gel, 2000 micron rotor, methylene chloride:methanol:ammonium hydroxide, 100:2.5:0.25) gave 235 mg (79%) of a clear colorless oil. Crystallization as the dihydrochloric acid salt from ethyl acetate/ethanol provided 235 mg of a white powder with mp>200° C. MS(m/e): 324(M+1).

Analysis for $C_{19}H_{23}Cl_2N_3O_2$:

Calcd: C, 57.48; H, 5.85; N,10.60; Found: C, 57,45; H, 5.85; N, 10.52.

Example 10

4-[3-(2,4-difluorobenzamidyl)benzoyl]-1-methylpiperidine hydrochloride

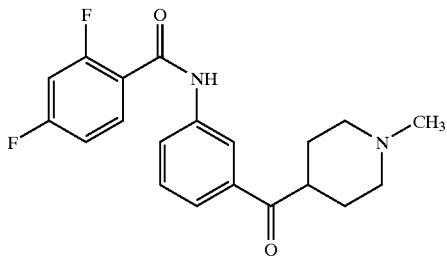

2,4 difluorobenzoyl chloride (100 μl, 0.82 mmol) was added to a mixture of 4-[3-aminobenzoyl]-1-methylpiperidine dihydrochloride (200 mg, 0.69 mmol), tetrahydrofuran (5 ml) and 1N sodium hydroxide solution (2.4 ml). The reaction mixture was stirred 24 h at room temperature. The reaction mixture was diluted with ethyl acetate and 1N sodium hydroxide solution then extracted with ethyl acetate. The ethyl acetate extracts were washed with brine, then dried over sodium sulfate. Solvent was removed under reduced pressure to give 220 mg. This mixture contained product and unreacted 4-[3-aminobenzoyl]-1-methylpiperidine. This mixture was dissolved in tetrahydrofuran and triethylamine (144 μl, 1.03 mmol) was added to the solution followed by 2,4 difluorobenzoyl chloride (100 μl, 0.82 mmol). The resulting mixture was stirred for 2 h at room temperature. The reaction mixture was diluted with ethyl acetate and 1N sodium hydroxide solution then extracted with ethyl acetate. The ethyl acetate extracts were washed with 1N sodium hydroxide solution, water, brine, then dried over sodium sulfate. Solvent was removed under reduced pressure to give an oil. The oil was dissolved in methylene chloride:methanol:ammonium hydroxide (100:5:0.5) and the resulting precipitate was filtered and discarded. Purification by radial chromatography (silica gel, 1000 micron rotor, methylene chloride:methanol:ammonium hydroxide, 100:5:0.5) gave 200 mg (81%) of a clear colorless oil. Crystallization as the hydrochloric acid salt from ethyl acetate/ethanol provided 185 mg of a white powder.

mp 181–3° C. MS(m/e): 359(M+1).

Analysis for $C_{20}H_{21}ClF_2N_2O_2$:

Calcd: C, 60.84; H, 5.36; N, 7.09; Found: C, 61.01; H, 5.28: N, 7.31.

Example 11

4-[3-(4-hydroxybenzamidyl)benzoyl]-1-methylpiperidine hydrochloride

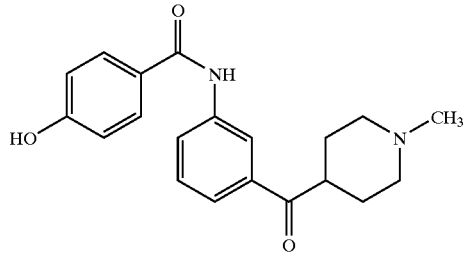

4-acetoxybenzoyl chloride (200 mg, 0.92 mmol) in tetrahydrofuran (10 mL) was added to 4-[3-aminobenzoyl]1-methylpiperidine (200 mg, 0.92 mmol) and triethylamine (0.5 mL, 3.6 mmol) in tetrahydrofuran (10 ml). The reaction mixture was stirred 64 h at room temperature. The reaction mixture was diluted with ethyl acetate and water then extracted with ethyl acetate. The ethyl acetate extracts were washed with water, brine, then dried over sodium sulfate. Solvent was removed under reduced pressure to give 493 mg of product. This product was dissolved in methanol (5 mL) and 5N sodium hydroxide solution (5 mL) and stirred until the hydrolysis of the acetate was complete. The solvent was removed under reduced pressure. The residue was dissolved in water and the pH of the solution was adjusted to 8–9 with 1N hydrochloric acid solution. This solution was extracted with chloroform/isopropanol (3:1) and dried over sodium sulfate. Solvent was removed under reduced pressure to give 270 mg of a foam.

Purification by flash chromatography (silica gel, 5% 2M ammonia in methanol/methylene chloride then 10% 2M ammonia in methanol/methylene chloride) gave 240 mg (77%). Crystallization as the hydrochloric acid salt from ethyl acetate/ethanol provided 220 mg of an off white powder.

Mp>200° C. MS(m/e): 339(M+1), 337(M−1).

Analysis for $C_{20}H_{23}ClN_2O_3$:

Calcd: C, 64.08; H, 6.18; N, 7.47; Found: C, 64.27; H, 6.40; N, 7.45.

Example 12

4-[3-(2-iodo-4-fluorobenzamidyl)benzoyl]-1-methylpiperidine hydrochloride

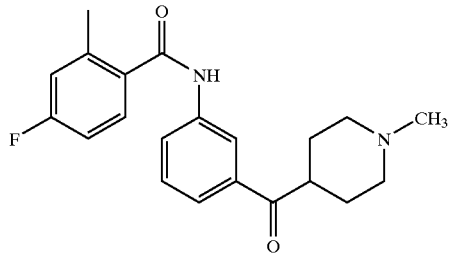

A mixture of 2-iodo-4-fluorobenzoic acid (194 mg, 0.73 mmol) and phosphorus pentachloride (152 mg, 0.73 mmol) in diethyl ether (5 mL) was stirred at room temperature for 2 h. The solvent was removed under reduced pressure to yield the 2-iodo-4-fluorobenzoyl chloride.

A solution of 2-iodo-4-fluorobenzoyl chloride in tetrahydrofuran (5 mL) was added to a solution of 4-[3-aminobenzoyl]-1-methylpiperidine ketone (145 mg, 0.66 mmol) and triethylamine (0.5 mL, 3.6 mmol) in tetrahydrofuran (5 ml). The reaction mixture was stirred 16 h at room temperature. The reaction mixture was diluted with ethyl acetate and water then extracted with ethyl acetate. The ethyl acetate extracts were washed with 0.2N sodium hydroxide solution, water, brine, then dried over sodium sulfate. The solvent was removed under reduced pressure. Prepurified by eluting through a small amount of silica gel (5% 2M ammonia in methanol/methylene chloride) then purified by radial chromatography (silica gel, 2000 micron rotor, 2.5% 2M ammonia in methanol/methylene chloride) gave 266 mg of a white foam. Crystallized as the hydrochloric acid salt from ethyl acetate/ethanol then recrystallized from ethyl acetate/methanol to provide 120 mg (48%) of an off white powder. mp>250° C. MS(m/e) 467(M+1), 465(M−1).

Analysis for $C_{20}H_{21}ClFIN_2O_2$:

Calcd: C, 47.78; H, 4.21; N, 5.57; Found: C, 47.71; H, 4.14; N, 5.44.

Example 13

4-[3-(4-fluorophenylsulfonyl)oxybenzoyl]-1-methylpiperidine

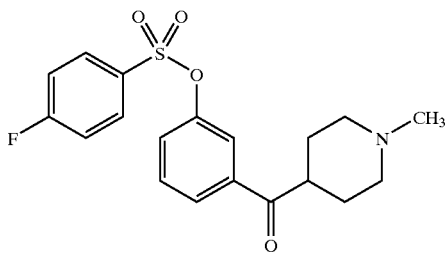

A solution of 4-fluorobenzenesulfonyl chloride (109 mg, 0.56 mmol) in THF (2.0 mL) was added to 4-[3-hydroxybenzoyl]-1-methylpiperidine(102 mg, 0.46 mmol) in 0.2 N sodium hydroxide (2.6 mL, 0.51 mmol) and THF (2.6 mL). The solution was stirred at room temperature for 2.5 h. The solution was diluted with ethyl acetate, washed with 0.2 N sodium hydroxide, water, brine, dried over sodium sulfate, and concentrated in vacuo to give 170 mg (97%). The hydrochloric acid salt was formed in ethyl acetate and concentrated in vacuo. The residue was dissolved in acetone and concentrated in vacuo to give a white foam. MS(m/e): 378(M+1).

Analysis for $C_{19}H_{21}ClFNO_4S$:

Calcd: C, 55.15; H, 5.11; N, 3.38; Found: C, 55.36; H, 5.67; N, 3.19.

Example 14

4-[3-(4-fluorobenzamidyl)benzoyl]-1-methylpiperidine hydrochloride

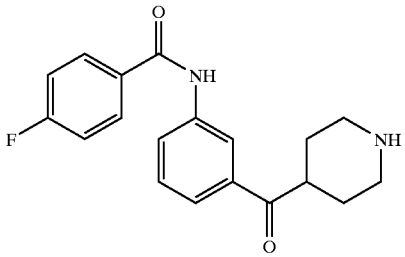

1-Chloroethyl chloroformate (435 μl, 4.0 mmol) was added dropwise to a 0° C. solution of 4-[3-(4-fluorobenzamidyl)benzoyl]-1-methylpiperidine (686 mg, 2.0 mmol) in 1,2-dichloroethane (15 ml). The reaction mixture was warmed to room temperature then heated to reflux for 1.5 h. An additional quantity of 1-chloroethyl chloroformate (400 μl, 3.7 mmol) was added and the reaction mixture was refluxed for 50 min. The reaction mixture was concentrated in vacuo. The residue was dissolved in methanol (15 mL) and heated to reflux for 2 h. The solvent was removed under vacuum to give 780 mg of a brown oil. Purification by radial chromatography (silica gel, 2000 micron rotor, methylene chloride:methanol:ammonium hydroxide, 95:5:0.5 then methylene chloride:methanol:ammonium hydroxide, 92.5:7.5:0.75) gave 220 mg (33%) of a white foam. Crystallization as the hydrochloride salt from ethyl acetate/ethanol gave a white solid. Mp>225° C. MS(m/e): 327(M+1).

Analysis for $C_{19}H_{20}ClFN_2O_2$:

Calcd: C, 62.90; H, 5.56; N, 7.72; Found: C, 62.71; H, 5.39; N, 7.62.

Example 15

4-[3-(4-fluorobenzamidyl)benzoyl]-1-[(1-isopropylpyraz-4-yl)ethyl]piperidine oxalate

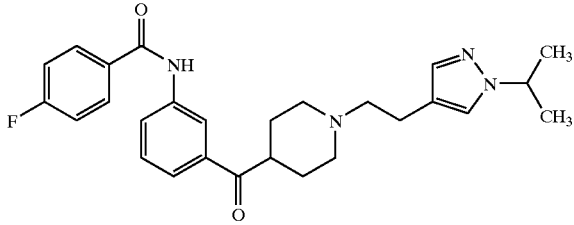

A mixture of 4-[3-(4-fluorobenzamidyl)benzoyl]-1-methylpiperidine (397 mg, 1.2 mmol), 1H-pyrazole-4-ethanol, 1-(1-methylethyl)-, methanesulfonate (396 mg, 1.7 mmol), and potassium carbonate (336 mg, 2.4 mmol) in dimethylformamide (20 mL) was heated to 80° C. for 21 h. The reaction mixture was cooled to ambient temperature and diluted with water and ice. This mixture was extracted with ethyl acetate/diethyl ether and the organic extracts were washed with water, brine, dried over sodium sulfate, and concentrated in vacuo to give 600 mg of a yellow oil.

Purification by radial chromatography (silica gel, 2000 micron rotor, methylene chloride:methanol:ammonium hydroxide, 97.5:2.5:0.25) gave 120 mg (21%) of a yellow oil. Crystallization as the oxalic acid salt from ethyl acetate gave 135 mg of a pale yellow powder. MS (m/e): 463(M+1), 461(M−1).

Analysis for $C_{29}H_{33}FN_4O_6$:

Calcd: C, 63.03; H, 6.02; N, 10.14; Found: C, 62.89; H, 6.29; N, 9.94.

Example 16

4-[3-(benzamidyl)benzoyl]-1-methylpiperidine

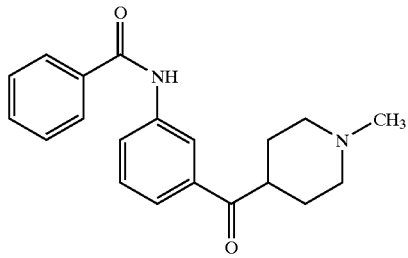

A mixture of 4-[3-aminobenzoyl]-1-methylpiperidine (25 mg, 0.115 mmol) and benzoyl chloride (39 μL, 0.336 mmol) in methylene chloride (1 mL) was mixed for 18 h at ambient temperature. The solution was diluted with 10% acetic acid in methanol and poured over a Varian Mega Bond Elut™ strong cation exchange column (Siegel, M. G.; Hahn, P. J.; Dressman, B. A.; Fritz, J. E.; Grunwell, J. R.; Kaldor, S. W. *Tetrahedron Lett*. 1997, 38, 3357–3360). The column was rinsed extensively with methanol to remove impurities, then treated with a 7M ammonia in methanol to elute the product from the column. The solvent was evaporated to give 37.6 mg (>100%) of the title compound.

MS(m/e): 323(M+1), 321(M−1).

The compounds of Examples 17 through 21 were prepared by the procedure described in detail in Example 16.

Example 17

4-[3-N'-(N-phenylmethylureido)benzoyl]-1-methylpiperidine

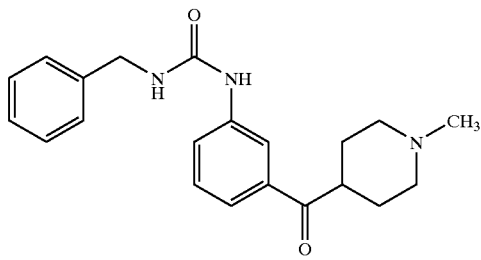

Beginning with 4-[3-aminobenzoyl]-1-methylpiperidine (50 mg, 0.229 mmol) and benzyl isocyanate (85 μL, 0.688 mmol), 79.1 mg (98%) of the title compound were recovered.

MS(m/e): 352(M+1), 350(M−1).

Example 18

4-[3-N'-(N-(4-fluorophenyl)thioureido)benzoyl]-1-methylpiperidine

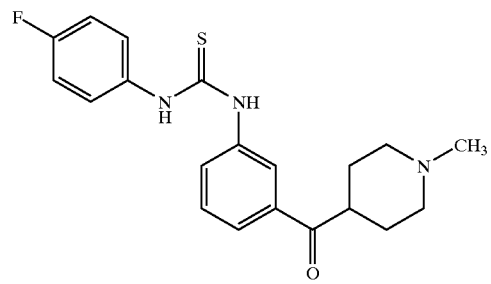

Beginning with 4-[3-aminobenzoyl]-1-methylpiperidine (50 mg, 0.229 mmol) and 4-fluorophenyl isothiocyanate (105 mg, 0.685 mmol), 87.5 mg (>100%) of the title compound were recovered.

MS(m/e): 372(M+1), 370(M−1).

Example 19

4-[3-(2-methoxybenzamidyl)benzoyl]-1-methylpiperidine

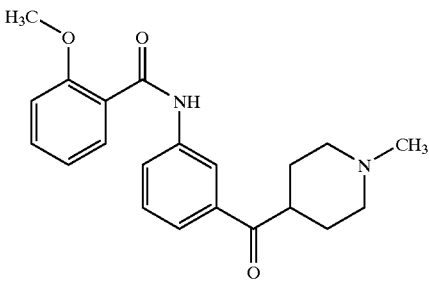

Beginning with 4-[3-aminobenzoyl]-1-methylpiperidine (50 mg, 0.229 mmol) and 2-methoxybenzoyl chloride (102 μl, 0.685 mmol), 62.6 mg (78%) of the title compound were recovered.

MS(m/e): 353(M+1) 351(M−1).

Example 20

4-[3-(4-fluorophenylsulfonamino)benzoyl]-1-methylpiperidine

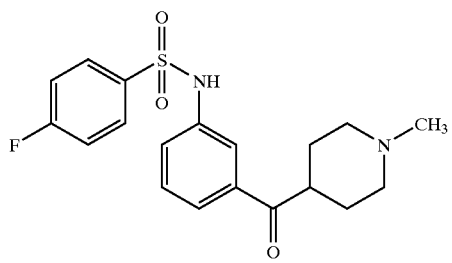

Beginning with 4-[3-aminobenzoyl]-1-methylpiperidine (50 mg, 0.229 mmol) and 4-fluorobenzenesulfonyl chloride (133 mg, 0.683 mmol), 80.4 mg (93%) of the title compound were recovered.

MS(m/e): 377(M+1), 375(M−1).

Example 21

4-[3-(phenylmethoxyamidyl)benzoyl]-1-methylpiperidine

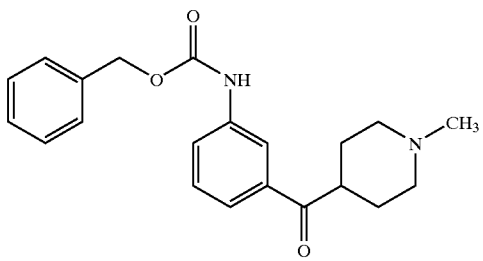

Beginning with 4-[3-aminobenzoyl]-1-methylpiperidine (50 mg, 0.229 mmol) and benzyl chloroformate (98 μl, 0.686 mmol), 77.3 mg (96%) of the title compound were recovered.

MS(m/e): 353(M+1), 351(M−1).

Example 22

4-[3-(2-bromobenzamidyl)benzoyl]-1-methylpiperidine

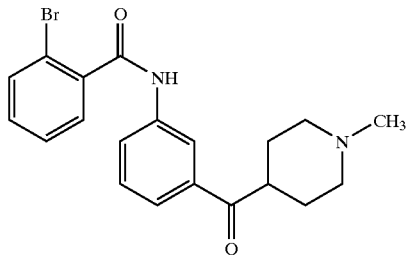

A mixture of 4-[3-aminobenzoyl]-1-methylpiperidine (50 mg, 0.229 mmol) and (piperidinomethyl)-polystyrene (100 mg, 0.260 mmol) in methylene chloride (1 mL) was allowed to stand for 5 min. To this mixture was added 2-bromobenzoyl chloride (151 mg, 0.687 mmol). The reaction mixture was mixed for 2 h at ambient temperature. The reaction mixture was filtered and the filter cake was rinsed with methanol. The filtrate solution was diluted with 10% acetic acid in methanol and poured over a Varian Mega Bond Elut™ strong cation exchange column (Siegel, M. G.; Hahn, P. J.; Dressman, B. A.; Fritz, J. E.; Grunwell, J. R.; Kaldor, S. W. *Tetrahedron Lett*. 1997, 38, 3357–3360). The column was rinsed with methanol to remove impurities, then treated with a 7M ammonia in methanol to elute the product from the column. The solvent was evaporated to give 45.6 mg (50%) of the title compound.

MS(m/e): 401, 403(M+1), 399, 401(M−1).

The compounds of Examples 23 through 40 were prepared by the procedure described in detail in Example 22.

Example 23

4-[3-(2-fluorobenzamidyl)benzoyl]-1-methylpiperidine

Beginning with 4-[3-aminobenzoyl]-1-methylpiperidine (50 mg, 0.229 mmol) and 2-fluorobenzoyl chloride (82 μl, 0.687 mmol), 76.8 mg (99%) of the title compound were recovered.

MS(m/e): 341(M+1), 339(M−1).

Example 24

4-[3-(2-chlorobenzamidyl)benzoyl]-1-methylpiperidine

Beginning with 4-[3-aminobenzoyl]-1-methylpiperidine (50 mg, 0.229 mmol) and 2-chlorobenzoyl chloride (87 μl, 0.687 mmol), 79.9 mg (98%) of the title compound were recovered.

MS(m/e): 357(M+1), 355(M−1).

Example 25

4-[3-(2-(trifluoromethyl)benzamidyl)benzoyl]-1-methylpiperidine

Beginning with 4-[3-aminobenzoyl]-1-methylpiperidine (50 mg, 0.229 mmol) and 2-(trifluoromethyl)benzoyl chloride (101 μl, 0.687 mmol), 81.9 mg (92%) of the title compound were recovered.

MS(m/e): 391(M+1), 389(M−1).

Example 26

4-[3-(2-methylbenzamidyl)benzoyl]-1-methylpiperidine

Beginning with 4-[3-aminobenzoyl]-1-methylpiperidine (50 mg, 0.229 mmol) and 2-methylbenzoyl chloride (90 μl, 0.687 mmol), 73.1 mg (95%) of the title compound were recovered.

MS(m/e): 337(M+1), 335(M−1).

Example 27

4-[3-(3-bromobenzamidyl)benzoyl]-1-methylpiperidine

Beginning with 4-[3-aminobenzoyl]-1-methylpiperidine (50 mg, 0.229 mmol) and 3-bromobenzoyl chloride (91 μl, 0.687 mmol), 29.3 mg (32%) of the title compound were recovered.

MS(m/e): 401, 403(M+1), 399, 401(M−1).

Example 28

4-[3-(3-chlorobenzamidyl)benzoyl]-1-methylpiperidine

Beginning with 4-[3-aminobenzoyl]-1-methylpiperidine (50 mg, 0.229 mmol) and 3-chlorobenzoyl chloride (120 mg, 0.687 mmol), 67.6 mg (83%) of the title compound were recovered.

MS(m/e): 357(M+1), 355(M−1).

Example 29

4-[3-(3-methoxybenzamidyl)benzoyl]-1-methylpiperidine

Beginning with 4-[3-aminobenzoyl]-1-methylpiperidine (50 mg, 0.229 mmol) and 3-methoxybenzoyl chloride (97 μl, 0.687 mmol), 78.6 mg (97%) of the title compound were recovered.

MS(m/e): 353(M+1), 351(M−1).

Example 30

4-[3-(3-(trifluoromethyl)benzamidyl)benzoyl]-1-methylpiperidine

Beginning with 4-[3-aminobenzoyl]-1-methylpiperidine (50 mg, 0.229 mmol) and 3-(trifluoromethyl)benzoyl chloride (104 μl, 0.687 mmol), 88.6 mg (99%) of the title compound were recovered.

MS(m/e): 391(M+1), 389(M−1).

Example 31

4-[3-(3-methylbenzamidyl)benzoyl]-1-methylpiperidine

Beginning with 4-[3-aminobenzoyl]-1-methylpiperidine (50 mg, 0.229 mmol) and 3-methylbenzoyl chloride (91 μl, 0.687 mmol), 74.0 mg (96%) of the title compound were recovered.

MS(m/e): 337(M+1), 335(M−1).

Example 32

4-[3-(4-fluorobenzamidyl)benzoyl]-1-methylpiperidine

Beginning with 4-[3-aminobenzoyl]-1-methylpiperidine (50 mg, 0.229 mmol) and 4-fluorobenzoyl chloride (81 μl, 0.687 mmol), 61.1 mg (78%) of the title compound were recovered.

MS(m/e): 341(M+1), 339(M−1).

Example 33

4-[3-(4-methoxybenzamidyl)benzoyl]-1-methylpiperidine

Beginning with 4-[3-aminobenzoyl]-1-methylpiperidine (50 mg, 0.229 mmol) and 4-methoxybenzoyl chloride (117 mg, 0.687 mmol), 81.5 mg (>100%) of the title compound were recovered.

MS(m/e): 353(M+1), 351(M−1).

Example 34

4-[3-(4-phenylbenzamidyl)benzoyl]-1-methylpiperidine

Beginning with 4-[3-aminobenzoyl]-1-methylpiperidine (50 mg, 0.229 mmol) and 4-biphenylcarbonyl chloride (150 mg, 0.687 mmol), 30.8 mg (34%) of the title compound were recovered.

MS(m/e): 399(M+1), 397(M−1).

Example 35

4-[3-(4-trifluoromethylbenzamidyl)benzoyl]-1-methylpiperidine

Beginning with 4-[3-aminobenzoyl]-1-methylpiperidine (50 mg, 0.229 mmol) and 4-(trifluoromethyl)benzoyl chloride (102 μl, 0.687 mmol), 88.0 mg (98%) of the title compound were recovered.

MS(m/e): 391(M+1), 389(M−1).

Example 36

4-[3-(4-methylbenzamidyl)benzoyl]-1-methylpiperidine

Beginning with 4-[3-aminobenzoyl]-1-methylpiperidine (50 mg, 0.229 mmol) and 4-methylbenzoyl chloride (91 μl, 0.687 mmol), 74.0 mg (96%) of the title compound were recovered.

MS(m/e): 337(M+1), 335(M−1).

Example 37

4-[3-(2-iodobenzamidyl)benzoyl]-1-methylpiperidine

Beginning with 4-[3-aminobenzoyl]-1-methylpiperidine (50 mg, 0.229 mmol) and 2-iodobenzoyl chloride (183 mg, 0.687 mmol), 16.0 mg (16%) of the title compound were recovered.

MS(m/e): 449(M+1), 447(M−1).

Example 38

4-[3-(2-nitrobenzamidyl)benzoyl]-1-methylpiperidine

Beginning with 4-[(3-aminobenzoyl]-1-methylpiperidine (50 mg, 0.229 mmol) and 2-nitrobenzoyl chloride (91 μl, 0.687 mmol) but the reaction mixture was mixed for 24 h at ambient temperature, 82.5 mg (98%) of the title compound were recovered.

MS(m/e): 368(M+1), 366(M−1).

Example 39

4-[3-(3-nitrobenzamidyl)benzoyl]-1-methylpiperidine

Beginning with 4-[3-aminobenzoyl]-1-methylpiperidine (50 mg, 0.229 mmol) and 3-nitrobenzoyl chloride (128 mg, 0.687 mmol), 17.4 mg (21%) of the title compound were recovered.

MS(m/e): 368(M+1), 366(M−1).

Example 40

4-[3-(3-cyanobenzamidyl)benzoyl]-1-methylpiperidine

Beginning with 4-[3-aminobenzoyl]-1-methylpiperidine (50 mg, 0.229 mmol) and 3-cyanobenzoyl chloride (114 mg, 0.687 mmol), 21.2 mg (27%) of the title compound were recovered.

MS(m/e): 348(M+1), 346(M−1).

Example 41

4-[3-(4-nitrobenzamidyl)benzoyl]-1-methylpiperidine

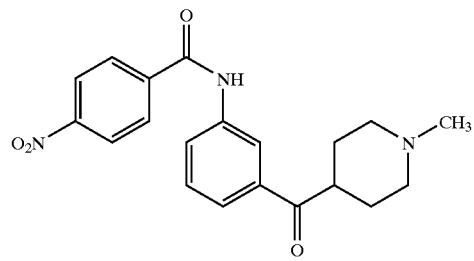

To a mixture of 4-[3-aminobenzoyl]-1-methylpiperidine (50 mg, 0.229 mmol) and (piperidinomethyl)-polystyrene (176 mg, 0.458 mmol) in tetrahydrofuran (1 mL) was added 4-nitrobenzoyl chloride (85 mg, 0.458 mmol) in tetrahydrofuran (1 mL). The reaction mixture was mixed for 18 h at ambient temperature. The reaction mixture was filtered and the filter cake was rinsed with methanol. The filtrate solution was diluted with 10% acetic acid in methanol and poured over a Varian Mega Bond Elut™ strong cation exchange column. The column was rinsed with methanol to remove impurities, then treated with a 7M ammonia in methanol to elute the product from the column. The solvent was evaporated to give 93 mg (>100%) of the title compound.

MS(m/e): 368 (M+1), 366 (M−1).

Analysis for $C_{20}H_{21}N_3O_4$:

Calcd: C, 65.38; H, 5.76; N, 11.44; Found: C, 65.47; H, 5.88; N, 11.40.

Example 42

4-[3-(3-fluorobenzamidyl)benzoyl]-1-methylpiperidine

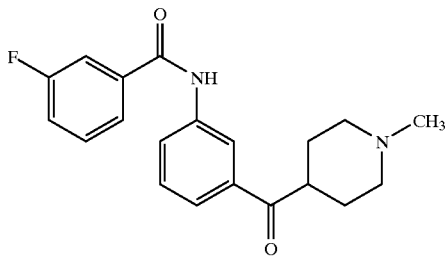

A mixture of 4-[3-aminobenzoyl]-1-methylpiperidine (25 mg, 0.115 mmol) and (piperidinomethyl)-polystyrene (50 mg, 0.130 mmol) in tetrahydrofuran (1 mL) was allowed to stand for 5 min. 3-fluorobenzoyl chloride (28 µL, 0.229 mmol) and tetrahydrofuran (1 mL) were added to the reaction mixture. The reaction mixture was mixed for 18 h at ambient temperature. The reaction mixture was filtered and the filter cake was rinsed with methanol. Glacial acetic acid (0.5 mL) was added to the filtrate solution and allowed to stand for 5 min. This mixture was poured over a Varian Mega Bond Elut™ strong cation exchange column. The column was rinsed with methanol to remove impurities, then treated with a 7M ammonia in methanol to elute the product from the column. The solvent was evaporated to give 43 mg (>100%) of the title compound.

MS(m/e): 341 (M+1), 339 (M−1).

The compounds of Examples 43 through 46 were prepared by the procedure described in detail in Example 42.

Example 43

4-[3-(4-bromobenzamidyl)benzoyl]-1-methylpiperidine

Beginning with 4-[3-aminobenzoyl]-1-methylpiperidine (25 mg, 0.115 mmol) and 4-bromobenzoyl chloride (50 mg, 0.229 mmol), 51.7 mg (>100%) of the title compound were recovered.

MS(m/e): 401, 403 (M+1), 399, 401 (M−1).

Example 44

4-[3-(4-chlorobenzamidyl)benzoyl]-1-methylpiperidine

Beginning with 4-[3-aminobenzoyl]-1-methylpiperidine (25 mg, 0.115 mmol) and 4-chlorobenzoyl chloride (29 µL, 0.229 mmol), 44.8 mg (>100%) of the title compound were recovered.

MS(m/e): 357(M+1), 355(M−1).

Example 45

4-[3-(4-iodobenzamidyl)benzoyl]-1-methylpiperidine

Beginning with 4-[3-aminobenzoyl]-1-methylpiperidine (25 mg, 0.115 mmol) and 4-iodobenzoyl chloride (61 mg, 0.229 mmol), 60.1 mg (>100%) of the title compound were recovered.

MS(m/e): 449(M+1), 447(M−1).

Example 46

4-[3-(4-cyanobenzamidyl)benzoyl]-1-methylpiperidine

Beginning with 4-[3-aminobenzoyl]-1-methylpiperidine (25 mg, 0.115 mmol) and 4-cyanobenzoyl chloride (38 mg, 0.229 mmol), 48.4 mg (>100%) of the title compound were recovered.

MS(m/e): 348(M+1), 346(M−1).

Example 47

4-[3-(2,3,4,5,6-pentafluorobenzamidyl)benzoyl]-1-methylpiperidine

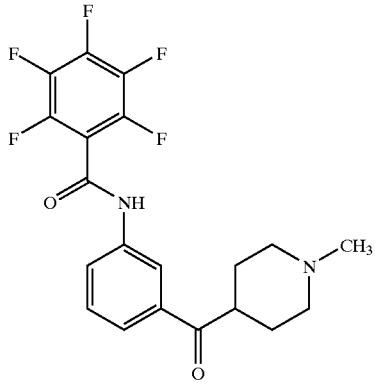

A mixture of 4-[3-aminobenzoyl]-1-methylpiperidine (25 mg, 0.115 mmol) and (piperidinomethyl)-polystyrene (100 mg, 0.260 mmol) in tetrahydrofuran (2 mL) was allowed to stand for 10 min. Pentafluorobenzoyl chloride (33 µL, 0.229 mmol) was added to the reaction mixture. The reaction mixture was mixed for 2 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed with methanol to remove impurities, then treated with a 7M ammonia in methanol to elute the product from the column. The solvent was evaporated to give 51 mg (>100%) of the title compound.

MS(m/e): 413 (M+1), 411 (M−1).

The compounds of Examples 48 through 66 were prepared by the procedure described in detail in Example 47.

Example 48

4-[3-(2,6-difluorobenzamidyl)benzoyl]-1-methylpiperidine

Beginning with 4-[3-aminobenzoyl]-1-methylpiperidine (25 mg, 0.115 mmol) and 2,6-difluorobenzoyl chloride (29 µL, 0.229 mmol) and mixing for 24 h, 46.6 mg (>100%) of the title compound were recovered.

MS(m/e): 359(M+1), 357(M−1).

Example 49

4-[3-(isopropylamidyl)benzoyl]-1-methylpiperidine-methyl(4-piperidyl))carbonyl]phenyl)propanamide Beginning with 4-[3-aminobenzoyl]-1-methylpiperidine (25 mg, 0.115 mmol) and isobutyryl chloride (24 µL, 0.229 mmol), 36.7 mg (>100%) of the title compound were recovered.

MS(m/e): 289(M+1), 287(M−1).

Example 50

4-[3-(phenylmethylamidyl)benzoyl]-1-methylpiperidine

Beginning with 4-[3-aminobenzoyl]-1-methylpiperidine (25 mg, 0.115 mmol) and phenylacetyl chloride (30 µL, 0.229 mmol), 43.8 mg (>100%) of the title compound were recovered.

MS(m/e): 337(M+1), 335(M−1).

Example 51

4-[3-(butylamidyl)benzoyl]-1-methylpiperidine

Beginning with 4-[3-aminobenzoyl]-1-methylpiperidine (25 mg, 0.115 mmol) and valeryl chloride (27 μL, 0.229 mmol), 38.8 mg (>100%) of the title compound were recovered.

MS(m/e): 303(M+1), 301(M−1).

Example 52

4-[3-(cyclohexylamidyl)benzoyl]-1-methylpiperidine

Beginning with 4-[3-aminobenzoyl]-1-methylpiperidine (25 mg, 0.115 mmol) and cyclohexanecarbonyl chloride (31 μL, 0.229 mmol), 41.1 mg (>100%) of the title compound were recovered.

MS(m/e): 329(M+1), 327(M−1).

Example 53

4-[3-(1-naphthylamidyl)benzoyl]-1-methylpiperidine

1-Naphthoyl chloride (44 mg, 0.229 mmol) in tetrahydrofuran (1 mL) and 4-[3-aminobenzoyl]-1-methylpiperidine (25 mg, 0.115 mmol) were mixed for 24 h and 45.6 mg (>100%) of the title compound were recovered.

MS(m/e): 373(M+1), 371(M−1).

Example 54

4-[3-(2-naphthylamidyl)benzoyl]-1-methylpiperidine

2-Naphthoyl chloride (44 mg, 0.229 mmol) in tetrahydrofuran (1 mL) and 4-[3-aminobenzoyl]-1-methylpiperidine (25 mg, 0.115 mmol) were mixed for 24 h and 45.6 mg (>100%) of the title compound were recovered.

MS(m/e): 373(M+1), 371(M−1).

Example 55

4-[3-(2,5-difluorobenzamidyl)benzoyl]-1-methylpiperidine

Beginning with 4-[3-aminobenzoyl]-1-methylpiperidine (25 mg, 0.115 mmol) and 2,5-difluorobenzoyl chloride (28 μL, 0.229 mmol), 44.7 mg (>100%) of the title compound were recovered.

MS(m/e): 359(M+1), 357(M−1).

Example 56

4-[3-(3,4-difluorobenzamidyl)benzoyl]-1-methylpiperidine

Beginning with 4-[3-aminobenzoyl]-1-methylpiperidine (25 mg, 0.115 mmol) and 3,4-difluorobenzoyl chloride (29 μL, 0.229 mmol) and mixing for 24 h, 45.6 mg (>100%) of the title compound were recovered.

MS(m/e): 359(M+1), 357(M−1).

Example 57

4-[3-(3,5-difluorobenzamidyl)benzoyl]-1-methylpiperidine

Beginning with 4-[3-aminobenzoyl]-1-methylpiperidine (25 mg, 0.115 mmol) and 3,5-difluorobenzoyl chloride (29 μL, 0.229 mmol) and mixing for 24 h, 46.1 mg (>100%) of the title compound were recovered.

MS(m/e): 359 (M+1), 357(M−1).

Example 58

4-[3-(2,3-difluorobenzamidyl)benzoyl]-1-methylpiperidine

Beginning with 4-[3-aminobenzoyl]-1-methylpiperidine (25 mg, 0.115 mmol) and 2,3-difluorobenzoyl chloride (28 μL, 0.229 mmol) and mixing for 24 h, 43.5 mg (>100%) of the title compound were recovered.

MS(m/e): 359(M+1), 357(M−1).

Example 59

4-[3-(4-trifluoromethoxybenzamidyl)benzoyl]-1-methylpiperidine

Beginning with 4-[3-aminobenzoyl]-1-methylpiperidine (25 mg, 0.115 mmol) and 4-(trifluoromethoxy)benzoyl chloride (36 μL, 0.229 mmol) and mixing for 24 h, 50.1 mg (>100%) of the title compound were recovered.

MS(m/e): 407(M+1), 405(M−1).

Example 60

4-[3-(2-trifluoromethoxybenzamidyl)benzoyl]-1-methylpiperidine

Beginning with 4-[3-aminobenzoyl]-1-methylpiperidine (25 mg, 0.115 mmol) and 2-(trifluoromethoxy)benzoyl chloride (37 μL, 0.229 mmol) and mixing for 24 h, 49.8 mg (>100%) of the title compound were recovered.

MS(m/e): 407(M+1), 405(M−1).

Example 61

4-[3-(2,3,6-trifluorobenzamidyl)benzoyl]-1-methylpiperidine

Beginning with 4-[3-aminobenzoyl]-1-methylpiperidine (25 mg, 0.115 mmol) and 2,3,6-trifluorobenzoyl chloride (30 μL, 0.229 mmol) and mixing for 24 h, 47.7 mg (>100%) of the title compound were recovered.

MS(m/e): 377(M+1), 375(M−1).

Example 62

4-[3-(2,4,5-trifluorobenzamidyl)benzoyl]-1-methylpiperidine

Beginning with 4-[3-aminobenzoyl]-1-methylpiperidine (25 mg, 0.115 mmol) and 2,4,5-trifluorobenzoyl chloride (29 μL, 0.229 mmol) and mixing for 24 h, 46.2 mg (>100%) of the title compound were recovered.

MS(m/e): 377(M+1), 375(M−1).

Example 63

4-[3-(3-trifluoromethoxybenzamidyl)benzoyl]-1-methylpiperidine

Beginning with 4-[3-aminobenzoyl]-1-methylpiperidine (25 mg, 0.115 mmol) and 3-(trifluoromethoxy)benzoyl chloride (37 μL, 0.229 mmol) and mixing for 24 h, 50.4 mg (>100%) of the title compound were recovered.

MS(m/e): 407(M+1), 405(M−1).

Example 64

4-[3-(2,4,6-trifluorobenzamidyl)benzoyl]-1-methylpiperidine

Beginning with 4-[3-aminobenzoyl]-1-methylpiperidine (25 mg, 0.115 mmol) and 2,4,6-trifluorobenzoyl chloride (30

47

μL, 0.229 mmol) and mixing for 24 h, 45.1 mg (>100%) of the title compound were recovered.

MS(m/e): 377(M+1), 375(M−1).

Example 65

4-[3-(2,3,4-trifluorobenzamidyl)benzoyl]-1-methylpiperidine

Beginning with 4-[3-aminobenzoyl]-1-methylpiperidine (25 mg, 0.115 mmol) and 2,3,4-trifluorobenzoyl chloride (29 μL, 0.229 mmol) and mixing for 24 h, 46.4 mg (>100%) of the title compound were recovered.

MS(m/e): 377(M+1), 375(M−1).

Example 66

4-[3-(2-chloro-4-fluorobenzamidyl)benzoyl]-1-methylpiperidine

Beginning with 4-[3-aminobenzoyl]-1-methylpiperidine (25 mg, 0.115 mmol) and 2-chloro-4-fluorobenzoyl chloride (32 μL, 0.229 mmol) and mixing for 24 h, 44.9 mg (>100%) of the title compound were recovered.

MS(m/e): 375(M+1), 373(M−1).

Example 67

4-[3-(2,3,4,5-tetrafluorobenzamidyl)benzoyl]-1-methylpiperidine

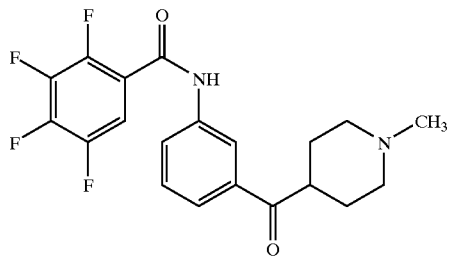

A mixture of 4-[3-aminobenzoyl]-1-methylpiperidine (25 mg, 0.115 mmol) and (piperidinomethyl)-polystyrene (100 mg, 0.260 mmol) in tetrahydrofuran (2 mL) was allowed to stand for 10 min. 2,3,4,5-Tetrafluorobenzoyl chloride (31 μL, 0.229 mmol) was added to the reaction mixture. The reaction mixture was mixed for 24 h at ambient temperature. The reaction mixture was filtered and the filter cake was rinsed with 7M ammonia in methanol. Glacial acetic acid (0.5 mL) was added to the filtrate solution and the solution was mixed. This mixture was poured over a Varian Mega Bond Elut™ strong cation exchange column. This purification was unsuccessful. The solvent was concentrated in vacuo. The residue was dissolved in water, basified with ammonium hydroxide, and extracted with methylene chloride. The organic extracts were washed with brine, glacial acetic acid (0.5 mL) was added to the organic extracts and the solution was mixed for 5 min. This mixture was poured over a Varian Mega Bond Elut™ strong cation exchange column. The column was rinsed with methanol to remove impurities, then treated with a 7M ammonia in methanol to elute the product from the column. The solvent was evaporated to give 43.7 mg (97%) of the title compound.

MS(m/e): 395(M+1), 393(M−1).

Example 68

4-[3-(3,4,5-trifluorobenzamidyl)benzoyl]-1-methylpiperidine

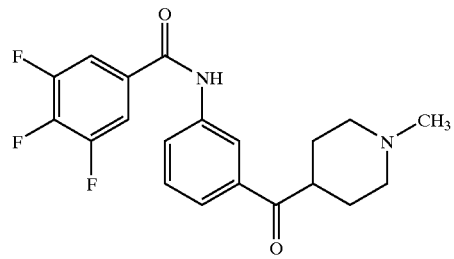

Following the example above and beginning with 4-[3-aminobenzoyl]-1-methylpiperidine (25 mg, 0.115 mmol) and 3,4,5-trifluorobenzoyl chloride (30 μL, 0.229 mmol), 42.5 mg (99%) of the title compound were recovered.

MS(m/e): 377(M+1), 375(M−1).

Example 69

4-[3-(aminoamidyl)benzoyl]-1-methylpiperidine

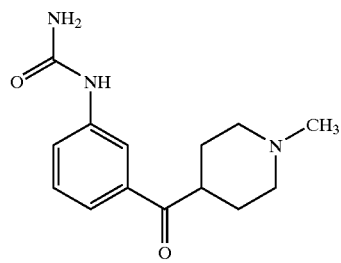

A mixture of 4-[3-aminobenzoyl]-1-methylpiperidine (25 mg, 0.115 mmol) and (piperidinomethyl)-polystyrene (100 mg, 0.260 mmol) in tetrahydrofuran (2 mL) was allowed to stand for 10 min. 4-fluorophenyl chloroformate (30 μL, 0.229 mmol) was added to the reaction mixture. The reaction mixture was mixed for 24 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed with methanol to remove impurities, then treated with a 7M ammonia in methanol to elute the product from the column. The solvent was removed under vacuum and the residue was purified by silica gel chromatography (methylene chloride:methanol:ammonium hydroxide, 100:5:0.5). The solvent was evaporated to give the title compound.

MS(m/e): 262 (M+1), 260 (M−1).

Example 70

4-[3-(phenylureido)benzoyl]-1-methylpiperidine

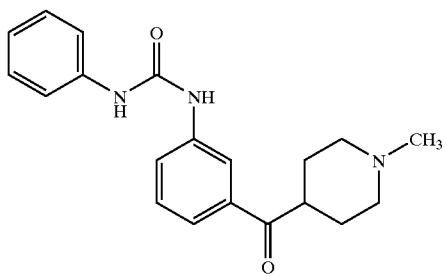

4-[3-aminobenzoyl]-1-methylpiperidine (25 mg, 0.115 mmol) and phenyl isocyanate (37 μL, 0.344 mmol) in methylene chloride (2 mL) were mixed for 72 h at ambient temperature. The solution was diluted with 10% acetic acid in methanol and poured over a Varian Mega Bond Elut™ strong cation exchange column. The column was rinsed extensively with methanol to remove impurities, then treated with a 2M ammonia in methanol to elute the product from the column. The solvent was evaporated and the residue was stirred with 5N sodium hydroxide solution (1 mL). The solvent was removed under vacuum and the residue was purified by silica gel chromatography (methylene chloride:methanol:ammonium hydroxide, 97.5:2.5:0.25 then 95:5:0.5). The solvent was evaporated to give 28.5 mg (74%) of the title compound.

MS(m/e): 338(M+1), 336(M−1).

Example 71

4-[3-(4-fluorophenylureido)benzoyl]-1-methylpiperidine

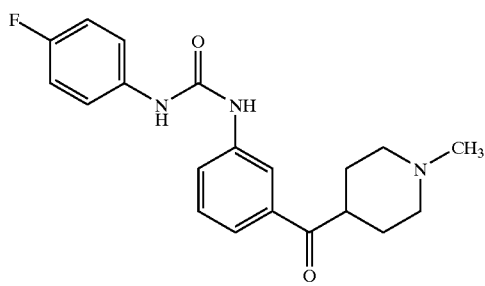

4-[3-aminobenzoyl]-1-methylpiperidine (25 mg, 0.115 mmol) and 4-fluorophenyl isocyanate (39 μL, 0.344 mmol) in methylene chloride (2 mL) were mixed for 72 h at ambient temperature. The solution was diluted with 10% acetic acid in methanol and poured over a Varian Mega Bond Elut™ strong cation exchange column. The column was rinsed extensively with methanol to remove impurities, then treated with a 2M ammonia in methanol to elute the product from the column. The solvent was evaporated and the residue was stirred with 5N sodium hydroxide solution (1 mL). The solvent was removed under vacuum and the residue was purified by silica gel chromatography (methylene chloride:methanol:ammonium hydroxide, 97.5:2.5:0.25 then 95:5:0.5). The solvent was evaporated to give 27.4 mg (67%) of the title compound.

MS(m/e): 356(M+1), 354(M−1).

Example 72

4-[3-(cyclohexylureido)benzoyl]-1-methylpiperidine

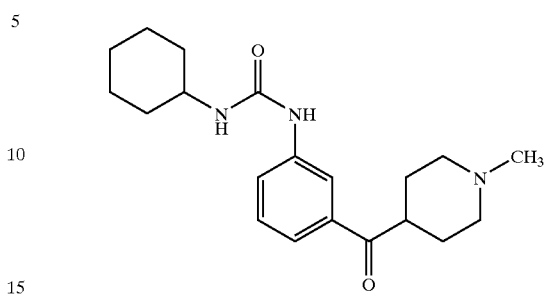

4-[3-aminobenzoyl]-1-methylpiperidine (25 mg, 0.115 mmol) and cyclohexyl isocyanate (44 μL, 0.344 mmol) in methylene chloride (2 mL) were mixed for 72 h at ambient temperature. The solution was diluted with 10% acetic acid in methanol and poured over a Varian Mega Bond Elut™ strong cation exchange column. The column was rinsed extensively with methanol to remove impurities, then treated with a 2M ammonia in methanol to elute the product from the column. The solvent was evaporated and the residue was dissolved in tetrahydrofuran (2 mL). Cyclohexyl isocyanate (44 μL, 0.344 mmol) and poly(4-dimethyaminopyridine) (82 mg, 0.115 mmol) were added and the reaction mixture was mixed for 5 days. The reaction mixture was filtered and the filter cake was washed with methanol. The solution was diluted with 10% acetic acid in methanol and poured over a Varian Mega Bond Elut™ strong cation exchange column. The column was rinsed extensively with methanol to remove impurities, then treated with a 2M ammonia in methanol to elute the product from the column. The solvent was evaporated to give 36.4 mg (93%) of the title compound.

MS(m/e): 344(M+1), 342(M−1).

The compounds of Examples 73 through 74 were prepared by the procedure described in detail in Example 72.

Example 73

4-[3-(phenylthioureido)benzoyl]-1-methylpiperidine

Beginning with 4-[3-aminobenzoyl]-1-methylpiperidine (25 mg, 0.115 mmol) and phenyl isothiocyanate (82 μL, 0.688 mmol), 40.5 mg (100%) of the title compound were recovered.

MS(m/e): 354(M+1), 352(M−1).

Example 74

4-[3-(benzylthioureido)benzoyl]-1-methylpiperidine

Beginning with 4-[3-aminobenzoyl]-1-methylpiperidine (25 mg, 0.115 mmol) and benzyl isothiocyanate (92 μL, 0.688 mmol), 37.6 mg (89%) of the title compound were recovered.

MS(m/e): 368(M+1), 366(M−1).

Example 75

4-[3-(phenoxyamidyl)benzoyl]-1-methylpiperidine

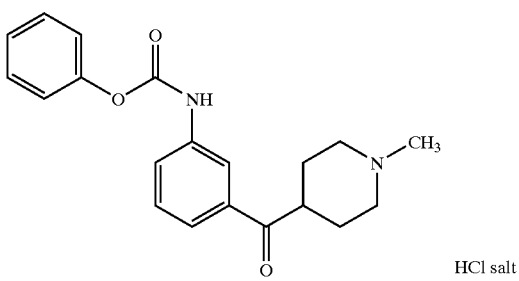

HCl salt

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Phenyl chloroformate (43 µL, 0.344 mmol) was added and the reaction mixture was mixed for 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M hydrochloric acid in methanol to elute the product from the column. The solvent was evaporated to give 38.9 mg (91%) of the title compound.

MS(m/e): 339(M+1), 337 (M−1).

Example 76

4-[3-(butoxyamidyl)benzoyl]-1-methylpiperidine

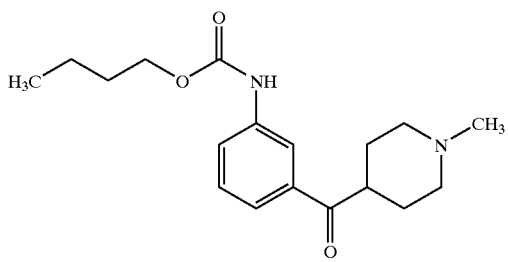

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Butyl chloroformate (44 µL, 0.344 mmol) was added and the reaction mixture was mixed for 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated to give 36.6 mg (100%) of the title compound.

MS(m/e): 319(M+1), 317(M−1).

Example 77

4-[3-(isopropylureido)benzoyl]-1-methylpiperidine

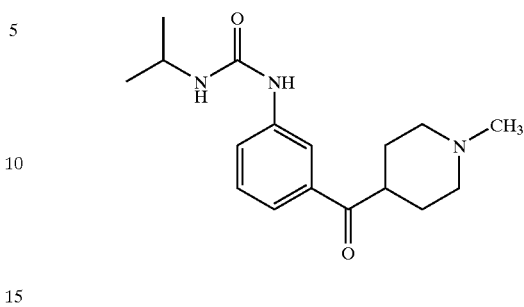

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Isopropyl isocyanate (34 µL, 0.344 mmol) was added and the reaction mixture was mixed for 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated and the residue was purified by silica gel chromatography (1–3% gradient, 2M ammonia in methanol:methylene chloride). The solvent was evaporated to give 21.8 mg (63%) of the title compound.

MS(m/e): 304(M+1), 302(M−1).

Example 78

4-[3-(methylureido)benzoyl]-1-methylpiperidine

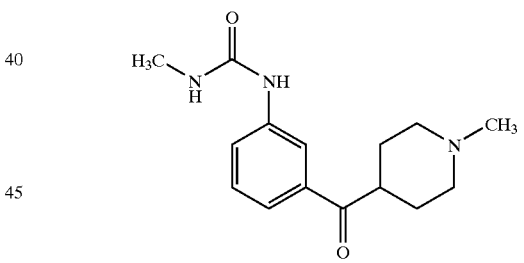

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Methyl isocyanate (20 µL, 0.344 mmol) was added and the reaction mixture was mixed for 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated and the residue was purified by silica gel chromatography (5% 2M ammonia in methanol:methylene chloride). The solvent was evaporated to give 28.1 mg (89%) of the title compound.

MS(m/e): 276(M+1), 274(M−1).

Example 79

4-[3-(methoxyamidyl)benzoyl]-1-methylpiperidine

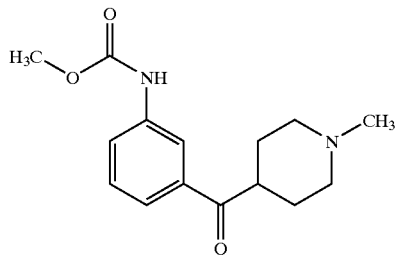

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Methyl chloroformate (27 µL, 0.344 mmol) was added and the reaction mixture was mixed for 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated and the residue was purified by silica gel chromatography (1–3% gradient, 2M ammonia in methanol:methylene chloride). The solvent was removed under vacuum. The residue was dissolved in methylene chloride (2 mL), polystyrene methylisocyanate (130 mg, 0.130 mmol, 1% crosslinked poly(styrene-co-divinylbenzene) was added, and the reaction mixture was mixed 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated to give 22.3 mg (70%) of the title compound.

MS(m/e): 277(M+1), 275(M−1).

Example 80

4-[3-(isopropoxyamidyl)benzoyl]-1-methylpiperidine

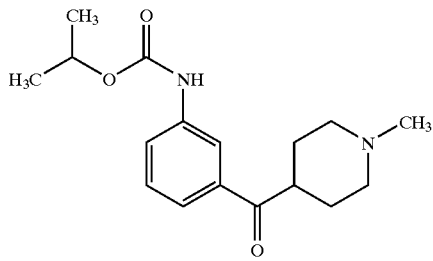

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Isopropyl chloroformate (344 µL, 0.344 mmol, 1M in toluene) was added and the reaction mixture was mixed a for 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated and the residue was purified by silica gel chromatography (5% 2M ammonia in methanol::methylene chloride). The solvent was evaporated. The residue was dissolved in methylene chloride (2 mL), polystyrene methylisocyanate (130 mg, 0.130 mmol, 1% crosslinked poly(styrene-co-divinylbenzene) was added, and the reaction mixture was mixed 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated to give 28.9 mg (83%) of the title compound.

MS(m/e): 305(M+1), 303(M−1).

Example 81

4-[3-(butylsulfonamino)benzoyl]-1-methylpiperidine

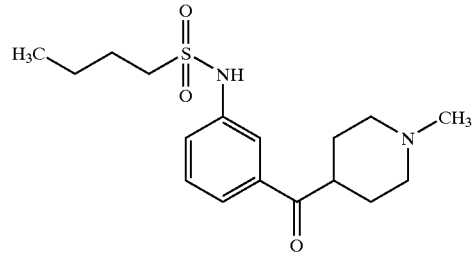

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Butanesulfonyl chloride (45 µL, 0.344 mmol) was added and the reaction mixture was mixed for 96 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated and the residue was purified by silica gel chromatography (1–3% gradient, 2M ammonia in methanol:methylene chloride). The solvent was removed under vacuum. The residue was dissolved in methylene chloride (2 mL), polystyrene methylisocyanate (130 mg, 0.130 mmol, 1% crosslinked poly(styrene-co-divinylbenzene) was added, and the reaction mixture was mixed 96 h at ambient temperature. An addition amount of polystyrene methylisocyanate (230 mg, 0.230 mmol) was added to the reaction mixture and mixing was continued for another 7 days. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated and the residue was purified by radial chromatography (silica gel, 1000 micron rotor, methylene chloride:2M ammonia in methanol, 100:2 then 100:4). The solvent was concentrated in vacuo to give 14.6 mg (38%) of the title compound.

MS(m/e): 339(M+1), 337(M−1).

Example 82

4-[3-(butylthioureido)benzoyl]-1-methylpiperidine

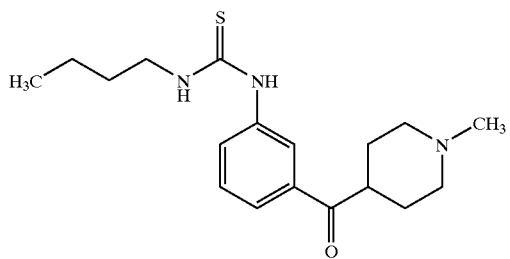

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Butyl isothiocyanate (41 μL, 0.344 mmol) was added and the reaction mixture was mixed for 96 h at ambient temperature. An addition amount of butyl isothiocyanate (100 μL, 0.829 mmol) was added to the reaction mixture and mixing was continued for another 6 days. Polystyrene methylisocyanate (230 mg, 0.230 mmol, 1% crosslinked poly(styrene-co-divinylbenzene) was added, and the reaction mixture was mixed 7 days at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated and the residue was purified by radial chromatography (silica gel, 1000 micron rotor, methylene chloride:2M ammonia in methanol, 100:2 then 100:4). The solvent was concentrated in vacuo to give 20.3 (53%) of the title compound.

MS(m/e): 334(M+1), 332(M−1).

Example 83

4-[3-(isopropylthioureido)benzoyl]-1-methylpiperidine

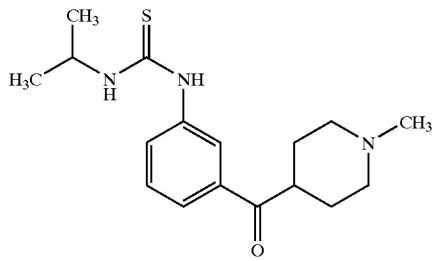

Following the example above and beginning with 4-[3-aminobenzoyl]-1-methylpiperidine (25 mg, 0.115 mmol) and isopropyl isothiocyanate (133 μL, 1.401 mmol), 15.6 mg (43%) of the title compound were recovered.

MS(m/e): 320(M+1), 318(M−1).

Example 84

4-[3-(butylureido)benzoyl]-1-methylpiperidine

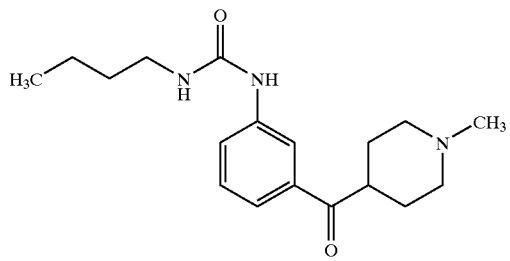

4-[3-aminobenzoyl]-1-methylpiperidine (25 mg, 0.115 mmol) and poly(4-vinyl pyridine) (50 mg, 0.400 mmol, 2% cross-linked) in tetrahydrofuran (2 mL) were allowed to stand 10 min. Butyl isocyanate (39 μL, 0.344 mmol) was added and the reaction mixture was mixed for 96 h at ambient temperature. An addition amount of butyl isocyanate(100 μL, 0.888 mmol) was added to the reaction mixture and mixing was continued for another 6 days. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed extensively with methanol to remove impurities, then treated with a 2M ammonia in methanol to elute the product from the column. The solvent was evaporated to give 44.4 mg (>100%) of the title compound.

MS(m/e): 318(M+1), 316(M−1).

Example 85

4-[3-(methylthioureido)benzoyl]-1-methylpiperidine

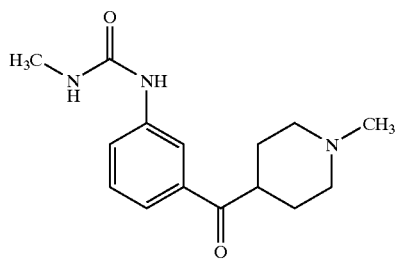

Following the example above and beginning with 4-[3-aminobenzoyl]-1-methylpiperidine (25 mg, 0.115 mmol) and methyl isothiocyanate (124 µL, 1.813 mmol), 22.0 mg (66%) of the title compound were recovered.

MS(m/e): 292(M+1), 290(M−1).

Example 86

4-[3-(thien-2-ylamidyl)benzoyl]-1-methylpiperidine

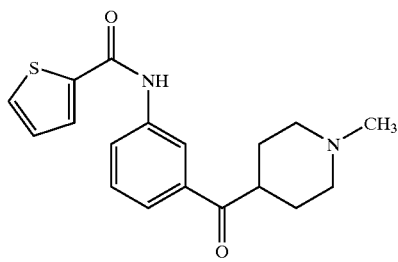

4-[3-aminobenzoyl]-1-methylpiperidine (30 mg, 0.137 mmol) and (piperidinomethyl)-polystyrene (106 mg, 0.276 mmol) in tetrahydrofuran (2 mL) was allowed to stand for 5 min. 2-Thiophenecarbonyl chloride (29 µL, 0.275 mmol) was added to the reaction mixture. The reaction mixture was mixed for 18 h at ambient temperature. The reaction mixture was filtered and the filter cake was rinsed with methanol. Glacial acetic acid (0.5 mL) was added to the filtrate solution and the solution was mixed. This mixture was poured over a Varian Mega Bond Elut™ strong cation exchange column. The column was rinsed with methanol to remove impurities, then treated with a 2M ammonia in methanol to elute the product from the column. The solvent was evaporated to give 44.9 mg (>100%) of the title compound.

MS(m/e): 329 (M+1), 327 (M−1).

Example 87

4-[3-(pyrid-3-ylamidyl)benzoyl]-1-methylpiperidine

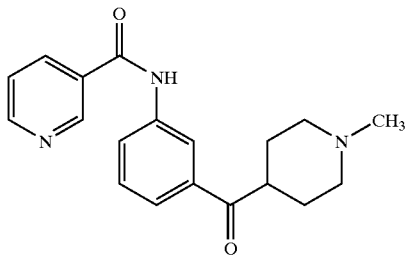

4-[3-aminobenzoyl]-1-methylpiperidine (30 mg, 0.137 mmol) and (piperidinomethyl)-polystyrene (250 mg, 0.650 mmol) in dimethylformamide (2 mL) was allowed to stand for 5 min. Nicotinoyl chloride hydrochloride (49.0 mg, 0.275 mmol) in dimethylformamide (1 mL) was added to the reaction mixture. The reaction mixture was mixed for 18 h at ambient temperature. The reaction mixture was filtered and the filter cake was rinsed with tetrahydrofuran. Glacial acetic acid (0.5 mL) was added to the filtrate solution and the solution was mixed. This mixture was poured over a Varian Mega Bond Elut™ strong cation exchange column. The column was rinsed with methanol to remove impurities, then treated with a 2M ammonia in methanol to elute the product from the column. The solvent was concentrated in vacuo and the residue was purified by radial chromatography (silica gel, 1000 micron rotor, 1–3% gradient, 2M ammonia in methanol:methylene chloride). The solvent was concentrated in vacuo to give 32.5 mg (88%) of the title compound.

MS(m/e): 324 (M+1), 322 (M−1).

Example 88

4-[3-(pyrid-2-ylamidyl)benzoyl]-1-methylpiperidine

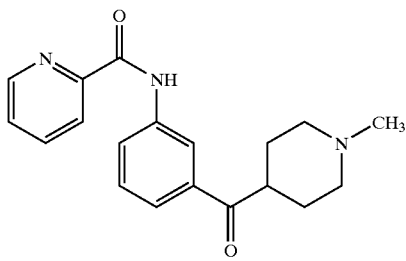

Following the example above and beginning with 4-[3-aminobenzoyl]-1-methylpiperidine (30 mg, 0.137 mmol) and picolinoyl chloride hydrochloride (49.0 mg, 0.275 mmol), 39.3 mg (>100%) of the title compound were recovered.

MS(m/e): 324 (M+1), 322 (M−1).

Example 89

2-amino-5-(4-fluorobenzamidyl)benzoyl)-1-methylpiperidine

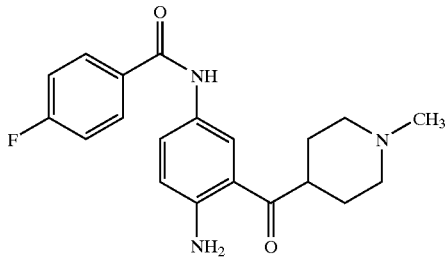

To a solution of 2-formamidyl-5-(4-fluorobenzamidyl)benzoyl)-1-methylpiperidine (500 mg, 1.3 mmol) in methanol (20 ml) was added 5N aqueous sodium hydroxide (2.6 ml, 13.0 mmol). The resulting reaction mixture was stirred at room temperature for 3 hours and 40 minutes then an additional amount of 5N aqueous sodium hydroxide (2.6 ml, 13.0 mmol) was added. The reaction mixture was stirred at room temperature for 1.5 hours, 5N aqueous sodium hydroxide (5.0 ml, 25.0 mmol) was added, and the mixture was heated at 45° C. for 1 hour. The solvent was removed under reduced pressure and the residue was dissolved in ethyl acetate. The ethyl acetate solution was washed with water and brine, dried over sodium sulfate, filtered and concentrated in vacuo to give 480 mg of a yellow oil. Purification by flash chromatography (silica gel, methylene chloride:methanol:ammonium hydroxide, 100:5:0.5) gave 460 mg (50.5%) of the title compound a yellow foam.

MS(m/e): 355 (M$^+$).

EA for $C_{22}H_{23}ClF_2N_2$:

Calcd: C, 67.95; H, 6.24; N, 11.82; Found: C, 67.33; H, 6.09; N, 11.58.

Experiment 90

4-(o/p/m-nitrobenzoyl)-1-trifluoromethylcarbonylpiperidines

The suspension of the commercially available 4-benzoylpiperidine hydrochloride (2.257 g, 0.01 mol) in trifluoroacetic anhydride (15 mL) was refluxed for 5 h. The reaction was monitored by TLC [silica gel/ethyl acetate—hexane (2:3)]. The cloudy solution was then allowed to stir for 16 h at room temperature. The reaction mixture was cooled to 5–6° C. (ice bath) and NH$_4$NO$_3$ (1.68 g, 0.021 mol) was added by portion in 45 min. The addition completed, the suspension was post-agitated for 1 h at 6–10° C. and then allowed to reach RT. The reaction was monitored by TLC [silica gel/ethyl acetate—hexane (2:3)]. The solution was concentrated under vacuum to give a yellowish liquid residue. The residue was dissolved in CH$_2$Cl$_2$ (60 mL) and the resulting organic solution was washed with demineralized H$_2$O (2×25 mL). The organic layer was dried over MgSO$_4$ (4 g), filtered and rota-evaporated to dryness. The yellowish oil was taken up with absolute ethanol (2×15 mL), concentrated under reduce pressure and dried under vacuum to obtain a yellow solid (3.12 g, 94%) of a mixture 4-(3-nitrobenzoyl)-1-trifluoromethylcarbonylpiperidine, 4-(2-nitrobenzoyl)-1-trifluoromethylcarbonylpiperidine, and 4-(4-nitrobenzoyl)-1-trifluoromethylcarbonylpiperidine (62/33/5), as determined by NMR.

Experiment 91

4-(o/p/m-nitrobenzoyl)-1-trifluoromethylcarbonylpiperidines 4-benzoylpiperidine hydrochloride (2.257 g, 0.01 mol) was refluxed for 7 h in trifluoroacetic anhydride (15 mL, 22.3 g, 0.106 mol). Then, the resulting solution was allowed to stir for 20 h at room temperature. To the cold reaction mixture (5° C.) was added dropwise (20 min) fuming HNO$_3$ (1.32 g, 0.87 mL, 0.021 mol) maintaining the T-mass at 6–7° C. The addition completed, the suspension was post-agitated for 1 h at 6–10° C. (reaction monitored by TLC [silica gel/ethyl acetate-hexane (2:3)]).

The suspension was warmed to RT for 20 h and the resulting solution was rota-evaporated under reduce pressure. The reddish residue was dissolved in CH$_2$Cl$_2$ (60 mL) which was washed with demineralized H$_2$O (2×25 mL). The organic layer was dried over MgSO$_4$ (5 g), filtered and concentrated to dryness. The yellowish oil was taken up with absolute ethanol (2×30 mL), concentrated under reduce pressure and dried under vacuum at 50° C. to give a yellow solid (3.2 g, 97%) of a mixture 4-(3-nitrobenzoyl)-1-trifluoromethylcarbonylpiperidine, 4-(2-nitrobenzoyl)-1-trifluoromethylcarbonylpiperidine, and 4-(4-nitrobenzoyl)-1-trifluoromethylcarbonylpiperidine (64/32/4), as determined by NMR.

Example 92

4-(o/m-nitrobenzoyl)-1-trifluoromethylcarbonylpiperidines

A mixture of 4-(3-nitrobenzoyl)-1-trifluoromethylcarbonylpiperidine, 4-(2-nitrobenzoyl)-1-trifluoromethylcarbonylpiperidine, and 4-(4-nitrobenzoyl)-1-trifluoromethylcarbonylpiperidine (64/32/4) (56.7 g, 0.172 mol) was warmed in isopropanol (280 mL) at 70° C. until complete dissolution. Then, the reddish solution was cooled to room temperature. Precipitation was observed at Tmass=46–47° C. Then the yellow suspension was post-agitated for 3 h at room temperature before filtration. The filtered yellow solid was washed with isopropanol (2×30 mL and n-pentane (50 mL). Drying at 50° C. under vacuum yielded 46 g (85%) of 4-(3-nitrobenzoyl)-1-trifluoromethylcarbonylpiperidine and 4-(2-nitrobenzoyl)-1-trifluoromethylcarbonylpiperidine [67(m):33(o)] mixture.

Example 93

4-(3-nitrobenzoyl)piperidine HCl 4-(3-nitrobenzoyl)-1-trifluoromethylcarbonylpiperidine and 4-(2-nitrobenzoyl)-1-trifluoromethylcarbonylpiperidine [67(m):33(o)] mixture (40.36 g, 0.122 mol) was heated with reflux in isopropanol (1.39 L) containing HCl 37% (209 mL) for 18 h. The reaction was monitored by TLC [silica gel/ethyl acetate-hexane (2:3)]. The resulting solution was allowed to cool to room temperature and the crystallization occurred at Tmass=35° C. Then the suspension was post-agitated for 3 h at room temperature. The precipitate was collected by filtration, washed with ethanol (100 mL) and ethyl ether (100 mL) and dried under vacuum at 50° C. to give pure 4-(3-nitrobenzoyl)piperidine HCl as a pale yellow solid (17.81 g, 54%).

m.p.=267.6° C.

The mother liquors were concentrated to dryness and the residue was dried under vacuum at 50° C. to give 15.23 g of an off-white solid 4-(2-nitrobenzoyl)piperidine and 4-3-nitrobenzoyl)piperidine composition (80/20).

EA for $C_{12}H_{14}N_2O_3$ HCl:

Calcd: C, 53.24; H, 5.58; N, 10.35; Found: C, 53.16; H, 5.69; N, 10.66.

Example 94

4-(3-nitrobenzoyl)piperidine HCl

To a suspension of 2.8 g (8.48 mol) of 4-(3-nitrobenzoyl)-1-trifluoromethylcarbonylpiperidine, 4-(2-nitrobenzoyl)-1- trifluoromethylcarbonylpiperidine, and 4-(4-nitrobenzoyl)-1-trifluoromethylcarbonylpiperidine mixture (62:33:5) in isopropanol (60 mL) was added HCl 37% (10 mL). The reaction mixture was refluxed for 8 h and rapidly a complete dissolution was observed. Then, the solution was allowed to cool to room temperature and post-agitated for 4 h. The precipitate was filtered, rinsed with isopropanol (2×5 mL) and ethyl ether (5 mL). Drying under vacuum at 50° C. afforded pure 4-(3-nitrobenzoyl)piperidine HCl (956 mg, 42%).

Example 95

4-(3-nitrobenzoyl)-1-trifluoromethylcarbonylpiperidine and 4-(2-nitrobenzoyl)-1-trifluoromethylcarbonylpiperidine 4-(3-nitrobenzoyl)-1-trifluoromethylcarbonylpiperidine (4.9 g (0.0148 mol)) and 4-(2-nitrobenzoyl)-1-trifluoromethylcarbonylpiperidine (67:33) were added to isopropanol (100 mL) and HCl 37% (15 mL). The suspension was refluxed for 10 h to complete the hydrolysis. The reaction was monitored by TLC [silica gel/ethyl acetate-hexane (2:3)]. The resulting yellow solution was allowed to cool to room temperature and the resulting suspension was post-agitated for 10 h. The reaction mixture was then concentrated under reduce pressure and the residue was dried under vacuum for 16 h at 50° C. 4 g (100%) of 4-(3-nitrobenzoyl)piperidine HCl and 4-(2-nitrobenzoyl)piperidine HCl mixture were isolated as a light colored solid.

Example 96

Purification of 4-(3-nitrobenzoyl)piperidine HCl

The suspension of 4-(3-nitrobenzoyl)piperidine HCl and 4-(2-nitrobenzoyl)piperidine HCl (67(m)/33(o)) mixture (720 mg, 2.66 mmol,) in absolute ethanol (42 mL) was refluxed for 1 h. Then, the reaction mixture was allowed to cool to room temperature and post-agitated for 3 h before filtration. The solid was filtered, washed with ethanol (5 mL) and ethyl ether (5 mL) and dried under vacuum at 50° C. for 16 h to yield 417 mg (58%) of pure 4-(3-nitrobenzoyl)piperidine HCl.

Example 97

4-(3-nitrobenzoyl)-1-trifluoromethylcarbonylpiperidine 1.25 g (0.046 mol) of 4-(3-nitrobenzoyl)piperidine HCl was refluxed for 4.5 h in trifluoroacetic anhydride (7.5 mL). The reaction was monitored by TLC [silica gel/AcOEt-hexane (40/60)]. The solution was allowed to cool to room temperature and the solution was concentrated under reduce pressure. The residue was taken up with isopropanol (2×5 mL) and concentrated to dryness to give 4-(3-nitrobenzoyl)-1-trifluoromethylcarbonylpiperidine as a light colored solid.

4-(3-nitrobenzoyl)-1-trifluoromethylcarbonylpiperidine was recrystallized in isopropanol (10 mL). The suspension was refluxed until complete dissolution and the solid was filtered at RT after a post-stirring of 18 h. The precipitate was successively washed with isopropanol (2 mL) and n-pentane (5 mL). Drying under reduced pressure at 50° C. gave 4-(3-nitrobenzoyl)-1-trifluoromethyl carbonylpiperidine as a white solid (1.43 g, 94%).

m.p.=110.0° C.

Example 98

4-(2-nitrobenzoyl)-1-trifluoromethylcarbonylpiperidine 4-(2-nitrobenzoyl)piperidine HCl and 4-(3-nitrobenzoyl)piperidine HCl (80:20) mixture (9.7 g, 0.0358 mol) was refluxed for 6 h in trifluoroacetic anhydride (55 mL). The reaction was monitored by TLC [silica gel/ethyl ether-hexane (96/4)]. The solution was allowed to stir overnight at room temperature. Then, the solution was concentrated under reduce pressure. The residue was taken up with isopropanol (2×50 mL), concentrated and dried under vacuum to give a 11.3 g (96%) of 4-(2-nitrobenzoyl)-1-trifluoromethylcarbonylpiperidine and 4-(3-nitrobenzoyl)-1-trifluoromethylcarbonylpiperidine mixture.

The 4-(2-nitrobenzoyl)-1-trifluoromethylcarbonylpiperidine and 4-(3-nitrobenzoyl)-1-trifluoromethylcarbonylpiperidine 80/20 mixture was recrystallized in isopropanol (1 g in 60 mL) to give with 74% yield the ortho derivative 4-(2-nitrobenzoyl)-1-trifluoromethylcarbonylpiperidine after drying under vacuum at 50° C. for 16 h.

m.p.=125.9° C.

Example 99

4-(2-nitrobenzoyl)piperidine HCl 4-(2-nitrobenzoyl)-1-trifluoromethylcarbonylpiperidine (5 g (0.0151 mol)) was refluxed for 13 h in isopropanol (100 mL) containing HCl 37% (25 mL). The reaction was monitored by TLC [silica gel/ethyl ether].

The resulting solution was allowed to cool to room temperature where precipitation was observed. Then, the suspension was stirred for 2 additional hours and filtered. The solid was washed with isopropanol (10 mL) and n-pentane (15 mL). 3.46 g (84%) of 4-(2-nitrobenzoyl)piperidine HCl were isolated after drying under vacuum at 50° C. for 16 h.

m.p.=239.1° C.

Example 100

4-(3-aminobenzoyl)piperidine HCl

A Parr bottle of 220 mL thermostated at 28–29° C. was charged with a suspension of Pd/C 10% (18.2 mg) in methanol (20 mL) followed by 4-(3-nitrobenzoyl)piperidine HCl (1 g 3.69 mmol). The reactor was placed under hydrogen atmosphere(40 PSI). The hydrogenation was complete within 1 hour. The catalyst was removed by filtration and rinsed with methanol (2×5 mL). The filtrate was rota-evaporated and the solid dried under vacuum at 50° C. for 8 hours to give 890 mg (100%) of crude 4-(3-aminobenzoyl)piperidine HCl.

4-(3-aminobenzoyl)piperidine HCl (11.51 g (47.8 mmol)) was then suspended in ethanol (147 mL) and refluxed for 1 h. The mixture was allowed to stir at RT for 2 h. Then, the precipitate was filtered and rinsed successively with ethanol (2×15 mL) and ethyl ether (30 mL). The solid was dried under vacuum at 50° C. for 16 h yielding 11.05 g (45.9 mmol) of purified 4-(3-aminobenzoyl) piperidine HCl with 96% yield.

m.p.=208–210° C.

Example 102

4-[3-(4-fluorobenzamidyl)benzoyl]piperidine HCl 4-(3-aminobenzoyl)piperidine HCl (10.87 g (45.15 mmol)) was suspended in absolute ethanol (220 mL) in presence of propylene oxide (3.185 g, 3.84 mL, 54.84 mmol) at room temperature for 15 min. p-fluorobenzoyl chloride (8.93 g, 6.65 mL, 56.44 mmol) was then added dropwise.

During the addition, a partial dissolution was observed before the formation of a thick precipitate. The temperature rose from 22° C. to 33° C. during the acylation. The suspension was post-agitated at room temperature for 4 h. Then, the precipitate was filtered, washed with ethanol (22 mL) and diethylether (40 mL). 15.38 g (94%) of 4-[3-(4-fluorobenzamidyl)benzoyl]piperidine HCl were obtained after drying at 50° C. under vacuum for 12 hours.

The compounds of this invention are useful for increasing activation of the 5-HT$_{1F}$ receptor. An increase in the activation of the 5-HT$_{1F}$ is useful for treating a variety of disorders which have been linked to decreased neurotransmission of serotonin in mammals, e.g., migraine headaches. For further instruction on the nexus between activation of the 5-HT$_{1F}$ and migraine, see the previously incorporated by reference U.S. Pat. No. 5,708,008.

To demonstrate the use of the compounds of this invention in the treatment of migraine, their ability to bind to the 5-HT$_{1F}$ receptor subtype was determined. The ability of the compounds of this invention to bind to the 5-HT$_{1F}$ receptor subtype was measured essentially as described in N. Adham, et al., *Proceedings of the National Academy of Sciences (USA)*, 90:408–412, 1993.

Membrane Preparation: Membranes were prepared from transfected Ltk-cells (transfected with the human 5-HT$_{1F}$ receptor sequence) which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford. *Anal. Biochem.*, 72:248–254, 1976.

Radioligand Binding: [$^3$H-5-HT] binding was performed using slight modifications of the 5-HT$_{1D}$ assay conditions reported by Herrick-Davis and Titeler (*J. Neurochem.*, 50:1624–1631, 1988) with the omission of masking ligands. Radioligand binding studies were achieved at 37° C. in a total volume of 250 µL of buffer (50 mM Tris, 10 mM MgCl$_2$, 0.2 mM EDTA, 10 µM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 µM 5-HT. Binding was initiated by the addition of 50 µL membrane homogenates (10–20 µg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation. *Biochem. Pharmacol.*, 22:3099–3108, 1973. All experiments were performed in triplicate. Representative compounds of this invention were found to have affinity for the 5-HT$_{1F}$ receptor as measured by the procedure described above.

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An E$_{max}$ is determined by dividing the inhibition of a test compound by the maximal effect and determining a percent inhibition. N. Adham, et al., supra,; R. L. Weinshank, et al., *Proceedings of the National Academy of Sciences (USA)*, 89:3630–3634, 1992; and the references cited therein.

Measurement of cAMP formation: Human 5-HT$_{1F}$ receptor transfected NIH3T3 cells (estimated Bmax from one point competition studies=488 fmol/mg of protein) were incubated in DMEM, 5 mm theophylline, 10 mM HEPES (4-[2-hydroxyethyl]-1-piperazineethanesulfonic acid) and 10 µM pargyline for 20 minutes at 37° C., 5% CO$_2$. Drug dose-effect curves were then conducted by adding 6 different final concentrations of drug, followed immediately by the addition of forskolin (10 µM). Subsequently, the cells were incubated for an additional 10 minutes at 37° C., 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 µM). The plates were stored at 4° C. for 15 minutes and then centrifuged for minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds of the invention shown to have affinity for the 5-HT$_{1F}$ receptor were tested and found to be agonists at the 5-HT$_{1F}$ receptor in the cAMP assay.

The type of formulation employed for the administration of the compounds employed in the methods of the present invention may be dictated by the particular compounds employed, the type of pharmacokinetic profile desired from the route of administration and the compound(s), and the state of the patient.

Formulations amenable to oral or injectable administration are prepared in a manner well known in the pharmaceutical art and comprise at least one active compound. See, e.g., REMINGTON'S PHARMACEUTICAL SCIENCES, (16th ed. 1980).

In general, a formulation of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

The following formulation examples are illustrative only and are not intended to limit the scope of the present invention. The term "active ingredients" refers to a compound of formula I.

| Formulation Example 1 Hard Gelatin Capsules | |
|---|---|
| Ingredient | Quantity (mg/capsule) |
| 4-[3-((3-bromophenyl)sulfonyloxy)benzoyl]-1-methylpiperidine | 30.0 |
| Starch | 305.0 |
| Magnesium stearate | 5.0 |

| Formulation Example 2 Tablet | |
|---|---|
| Ingredient | Quantity (mg/tablet) |
| 4-[3-((4-iodophenyl)sulfonyloxy)benzoyl]-1-methylpiperidine | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

| Formulation Example 3 Dry Powder Inhaler | |
|---|---|
| Ingredient | Weight % |
| 4-[3-(3-nitrophenylthioureido)benzoyl]-1-methylpiperidine | 5 |
| Lactose | 95 |

The active ingredient is mixed with the lactose and the mixture is added to a dry powder inhaling appliance.

| Formulation Example 4 Tablet | |
|---|---|
| Ingredient | Quantity (mg/tablet) |
| 4-[3-(fur-2-ylthioureido)benzoyl]-1-methylpiperidine | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C.–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Formulation Example 5 Capsules | |
|---|---|
| Ingredient | Quantity (mg/capsule) |
| 4-[3-(pyridin-4-ylthioureido)benzoyl]-1-methylpiperidine | 40.0 |
| Starch | 109.0 |
| Magnesium stearate | 1.0 |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6
Suppositories

| Ingredient | Amount |
| --- | --- |
| 4-[3-(3-nitrophenylsulfonamino)benzoyl]-1-methylpiperidine | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7
Suspensions

| Ingredient | Amount |
| --- | --- |
| 4-[3-(pyrid-3-ylureido)benzoyl]-1-methylpiperidine | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and color | q.v. |
| purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8
Capsules

| Ingredient | Quantity (mg/capsule) |
| --- | --- |
| 4-[3-(2-hydroxyphenylsulfonamino)benzoyl]-1-methylpiperidine | 15.0 |
| Starch | 407.0 |
| Magnesium stearate | 3.0 |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9
Intravenous Formulation

| Ingredient | Quantity |
| --- | --- |
| 4-[3-(4-fluorophenylsulfonamino)benzoyl]-1-methylpiperidine | 250.0 mg |
| Isotonic saline | 1000 ml |

Formulation Example 10
Topical Formulation

| Ingredient | Quantity |
| --- | --- |
| 4-[3-((2-bromophenyl)amidyl)benzoyl]-1-methylpiperidine | 1–10 g |
| Emulsifying wax | 30 g |
| Liquid paraffin | 20 g |
| White soft paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11
Sublingual or Buccal Tablets

| Ingredient | Quantity (mg/tablet) |
| --- | --- |
| 4-[3-(thiophen-2-ylsulfonamino)benzoyl]-1-methylpiperidine | 10.0 |
| Glycerol | 210.5 |
| Water | 143.0 |
| Sodium citrate | 4.5 |
| Polyvinyl alcohol | 26.5 |
| Polyvinylpyrrolidone | 15.5 |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

While it is possible to administer a compound employed in the methods of this invention directly without any formulation, the compounds are usually administered in the form of pharmaceutical compositions comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

What is claimed is:

1. A compound of Formula I:

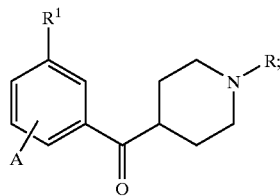

or a pharmaceutical acid addition salt thereof, where;

A is hydrogen, halo, $NH_2$, or $—CF_3$;

R is hydrogen, $C_1-C_4$ alkyl, $C_3-C_6$ alkenyl, $C_3-C_6$ alkynyl, or $(C_1-C_6$ alkyl$)-Ar^1$;

$R^1$ is NH—$R^2$—$R^3$;

Ar, $Ar^1$, $Ar^2$, $Ar^3$, and $Ar^4$ are an optionally substituted phenyl or optionally substituted heteroaryl;

$R^2$ is —CO—;

$R^3$ is $Ar^3$;

wherein substituted phenyl is phenyl mono-substituted with a substituent selected from the group consisting of halo, nitro, cyano, amino, trifluoromethyl, trifluoromethoxy, phenyl, benzoyl, $C_1-C_6$ alkyl, $C_1-C_6$ alkoxy, $(C_1-C_4$ alkyl$)S(O)_n$, $(C_1-C_4$ alkyl$)_2$ amino, $C_1-C_4$ acyl, or two or three substituents independently selected from the group consisting of halo, nitro, trifluoromethyl, $C_1-C_4$ alkyl, and $C_1-C_4$ alkoxy, n is 0, 1, or 2;

heteroaryl is an aromatic or benzofused aromatic 5 or 6 membered ring containing from 1 to 3 heteroatoms selected from the group consisting of nitrogen, oxygen and sulfur;

substituted heteroaryl is heteroaryl substituted with up to three substituents selected from the group consisting of halo, cyano, nitro, hydroxy, $C_1-C_4$ alkoxy, $C_1-C_4$ alkyl, $(C_1-C_4$ alkyl$)-S(O)_n$—, and phenyl-$S(O)_n$—;

substituted alkyl is alkyl substituted from 1 to 3 times independently with a substituent selected from the group consisting of halo, hydroxy, phenyl, 2-phenylethylen-1-yl, diphenylmethyl, naphthyl, substituted phenyl, aryloxy, heterocycle, heteroaryloxy, $C_2-C_6$ alkenyl, $C_2-C_6$ alkynyl, $C_3-C_8$ cycloalkyl, $C_1-C_4$ alkoxy, $C_1-C_4$ alkoxycarbonyl, phenyl$(C_1-C_4$ alkyl$)$, substituted phenyl$(C_1-C_4$ alkyl$)$, and benzofused $C_4-C_8$ cycloalkyl; and heterocycle is aromatic or non-aromatic 5 or 6 membered ring containing from 1 to 3 heteroatoms selected from the group consisting of nitrogen, oxygen, and sulfur, said ring being optionally benzofuzed and said ring or benzofused ring being optionally substituted with up to three substituents selected from the groups consisting of halo, $C_1-C_4$ alkoxy, $C_1-C_4$ alkyl, cyano, nitro, hydroxy, $(C_1-C_4$ alkyl$)-S(O)_n$—, and phenyl-$S(O)_n$—.

2. The compound of claim 1 wherein A is hydrogen.

3. The compound of claim 1 wherein R is methyl.

4. The compound of claim 1 wherein $Ar^3$ is 4-fluorophenyl.

5. The compound of claim 4 wherein $Ar^3$ is 4-fluorophenyl additionally mono- or disubstituted.

6. The compound of claim 5 wherein $Ar^3$ is selected from the group consisting of 2-iodo-4-fluorophenyl, 2-bromo-4-fluorophenyl, 2-chloro-4-fluorophenyl, 2,4-difluorophenyl, and 2-methyl-4-fluorophenyl, and 2,4,6-trifluorophenyl.

7. A pharmaceutical formulation comprising a compound of I:

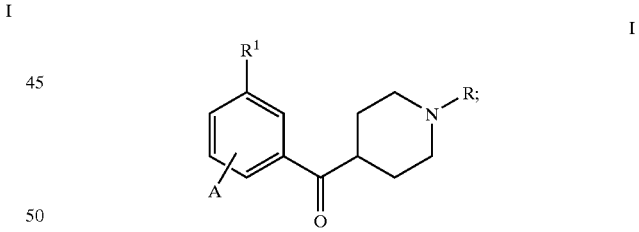

or a pharmaceutical acid addition salt thereof, where;

A is hydrogen, halo, $NH_2$, or $—CF_3$;

R is hydrogen, $C_1-C_4$ alkyl, $C_3-C_6$ alkenyl, $C_3-C_6$ alkynyl, or $(C_1-C_6$ alkyl$)-Ar^1$;

$R^1$ is —NH—$R^2$—$R^3$;

Ar, $Ar^1$, $Ar^2$, $Ar^3$, and $Ar^4$ are an optionally substituted phenyl or optionally substituted heteroaryl;

$R^2$ is —CO—;

$R^3$ is $Ar^3$;

wherein substituted phenyl is phenyl mono-substituted with a substituent selected from the group consisting of halo, nitro, cyano, amino, trifluoromethyl, trifluoromethoxy, phenyl, benzoyl, $C_1-C_6$ alkyl, $C_1-C_6$ alkoxy, $(C_1-C_4$ alkyl$)S(O)_n$, $(C_1-C_4$ alkyl$)_2$ amino, $C_1$–$C_4$ acyl, or two or three substituents independently selected from the group consisting of halo, nitro, trifluoromethyl, $C_1$–$C_4$ alkyl, and $C_1$–$C_4$ alkoxy;

n is 0, 1, or 2;

heteroaryl is an aromatic or benzofused aromatic 5 or 6 membered ring containing from 1 to 3 heteroatoms selected from the group consisting of nitrogen, oxygen and sulfur;

substituted heteroaryl is heteroaryl substituted with up to three substituents selected from the group consisting of halo, cyano, nitro, hydroxy, $C_1$–$C_4$ alkoxy, $C_1$–$C_4$ alkyl, ($C_1$–$C_4$ alkyl)-S(O)$_n$—, and phenyl-S(O)$_n$—;

substituted alkyl is alkyl substituted from 1 to 3 times independently with a substituent selected from the group consisting of halo, hydroxy, phenyl, 2-phenylethylen-1-yl, diphenylmethyl, naphthyl, substituted phenyl, aryloxy, heterocycle, heteroaryloxy, $C_2$–$C_6$ alkenyl, $C_2$–$C_6$ alkynyl, $C_3$–$C_8$ cycloalkyl, $C_1$–$C_4$ alkoxy, $C_3$–$C_4$ alkoxycarbonyl, phenyl($C_1$–$C_4$ alkyl), substituted phenyl($C_1$–$C_4$ alkyl), and benzofused $C_4$–$C_8$ cycloalkyl; and heterocycle is aromatic or non-aromatic 5 or 6 membered ring containing from 1 to 3 heteroatoms selected from the group consisting of nitrogen, oxygen, and sulfur, said ring being optionally benzofused and said ring or benzofused ring being optionally substituted with up to three substituents selected from the groups consisting of halo, $C_1$–$C_4$ alkoxy, $C_1$–$C_4$ alkyl, cyano, nitro, hydroxy, ($C_1$–$C_4$ alkyl)-S(O)$_n$—, and phenyl-S(O)$_n$—.

8. A process of making the compounds of formula I(a):

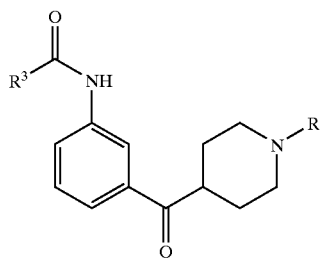

I(a)

wherein $R^3$ is hydrogen, optionally substituted $C_1$–$C_6$ alkyl, $Ar^3$, —$NR^5R^6$, or $OR^5$;

$R^5$ and $R^6$ are independently hydrogen, optionally substituted $C_1$–$C_8$ alkyl, or $Ar^4$; or $R^6$ and $R^5$ combine, together with the nitrogen atom to which they are attached, to form a pyrrolidine, piperidine, piperazine, 4-substituted piperazine, morpholine or thiomorpholine ring; and $Ar^3$ and $Ar^4$ are independently an optionally substituted phenyl or optionally substituted heteroaryl;

wherein substituted phenyl is phenyl mono-substituted with a substituent selected from the group consisting of halo, nitro, cyano, amino, trifluoromethyl, trifluoromethoxy, phenyl, benzoyl, $C_1$–$C_6$ alkyl, $C_1$–$C_6$ alkoxy, ($C_1$–$C_4$ alkyl)S(O)$_n$, ($C_1$–$C_4$ alkyl)$_2$ amino, $C_1$–$C_4$ acyl, or two or three substituents independently selected from the group consisting of halo, nitro, trifluoromethyl, $C_1$–$C_4$ alkyl, and $C_1$–$C_4$ alkoxy;

n is 0, 1, or 2;

heteroaryl is an aromatic or benzofused aromatic 5 or 6 membered ring containing from 1 to 3 heteroatoms selected from the group consisting of nitrogen, oxygen and sulfur;

substituted heteroaryl is heteroaryl substituted with up to three substituents independently selected from the group consisting of halo, cyano, nitro, hydroxy, $C_1$–$C_4$ alkoxy, $C_1$–$C_4$ alkyl, ($C_1$–$C_4$ alkyl)S(O)$_n$—, and phenyl-S(O)$_n$—;

substituted alkyl is alkyl substituted from 1 to 3 times independently with a substituent selected from the group consisting of halo, hydroxy, phenyl, 2-phenylethylen-1-yl, diphenylmethyl, naphthyl, substituted phenyl, aryloxy, heterocycle, heteroaryloxy, $C_2$–$C_6$ alkenyl, $C_2$–$C_6$ alkynyl, $C_3$–$C_8$ cycloalkyl, $C_1$–$C_4$ alkoxy, $C_1$–$C_4$ alkoxycarbonyl, phenyl($C_1$–$C_4$ alkyl), substituted phenyl($C_1$–$C_4$ alkyl), and benzofused $C_4$–$C_8$ cycloalkyl;

heterocycle is aromatic or non-aromatic 5 or 6 membered ring containing from 1 to 3 heteroatoms selected from the group consisting of nitrogen, oxygen, and sulfur, said ring being optionally benzofused and said ring or benzofused ring being substituted with up to three substituents selected independently from the groups consisting of halo, $C_1$–$C_4$ alkoxy, $C_1$–$C_4$ alkyl, cyano, nitro, hydroxy, ($C_1$–$C_4$ alkyl)-S(O)$_n$—, and phenyl-S(O)$_n$—;

comprising:
(a) protecting 4-benzoylpiperidine hydrochloride to form an N-protected 4-benzoylpiperidine hydrochloride;
(b) nitrating the N-protected 4-benzoylpiperidine hydrochloride to form a mixture of N-protected 4-(mono nitrobenzoyl)piperidines;
(c) deprotecting the N-protected 4-(mononitrobenzoyl)-piperidine mixture to form a mixture of 4-(mononitrobenzoyl)piperidines;
(d) separating the 4-(3-nitrobenzoyl)piperidine from the mixture of 4-(mononitrobenzoyl)piperidines;
(e) reducing the 4-(3-nitrobenzoyl)piperidine to form 4-(3-aminobenzoyl)piperidine; and
(f) acylating the 4-(3-aminobenzoyl)piperidine.

9. The process of claim 8 wherein steps a) and b) are combined.

10. The process of claim 8 wherein the source of the protecting group of step a) is trifluoroacetic anhydride.

11. The process of claim 8 wherein the N-protected 4-benzoylpiperidine hydrochloride is nitrated with ammonium nitrate.

12. The process of claim 10 wherein the N-protected 4-benzoylpiperidine hydrochloride is nitrated with ammonium nitrate.

13. A method for treating migraine in a mammal comprising administering to a mammal in need of such treatment an effective amount of a compound of formula I:

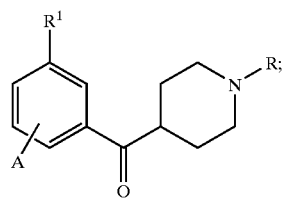

I or a pharmaceutical acid addition salt thereof, where;

A is hydrogen, halo, $NH_2$, or —$CF_3$;

R is hydrogen, $C_1$–$C_4$ alkyl, $C_3$–$C_6$ alkenyl, $C_3$–$C_6$ alkynyl, or ($C_1$–$C_6$ alkyl)-$Ar^1$;

R¹ is —NH—R²—R³ or —OSO₂Ar²;

Ar, Ar¹, Ar², Ar³, and Ar⁴ are an optionally substituted phenyl or optionally substituted heteroaryl;

R² is —CO—, —CS—, or —SO₂—;

R³ is hydrogen, optionally substituted C₁–C₆ alkyl, Ar³, —NR⁵R⁶, or OR⁵; provided R³ is not hydrogen if R² is either —CS— or —SO₂—;

R⁴ is hydrogen, optionally substituted C₁–C₆ alkyl, or Ar; and

R⁵ and R⁶ are independently hydrogen, optionally substituted C₁–C₈ alkyl, Ar⁴; or R⁶ and R⁵ combine, together with the nitrogen atom to which they are attached, to form a pyrrolidine, piperidine, piperazine, 4-substituted piperazine, morpholine or thiomorpholine ring;

wherein substituted phenyl is phenyl mono-substituted with a substituent selected from the group consisting of halo, nitro, cyano, amino, trifluoromethyl, trifluoromethoxy, phenyl, benzoyl, C₁–C₆ alkyl, C₁–C₆ alkoxy, (C₁–C₄ alkyl)S(O)ₙ, (C₁–C₄ alkyl)₂ amino, C₁–C₄ acyl, or two or three substituents independently selected from the group consisting of halo, nitro, trifluoromethyl, C₁–C₄ alkyl, and C₁–C₄ alkoxy;

n is 0, 1, or 2;

heteroaryl is an aromatic or benzofused aromatic 5 or 6 membered ring containing from 1 to 3 heteroatoms selected from the group consisting of nitrogen, oxygen and sulfur;

substituted heteroaryl is heteroaryl substituted with up to three substituents selected from the group consisting of halo, cyano, nitro, hydroxy, C₁–C₄ alkoxy, C₁–C₄ alkyl, (C₁–C₄ alkyl)-S(O)ₙ—, and phenyl-S(O)ₙ—;

substituted alkyl is alkyl substituted from 1 to 3 times independently with a substituent selected from the group consisting of halo, hydroxy, phenyl, 2-phenylethylen-1-yl, diphenylmethyl, naphthyl, substituted phenyl, aryloxy, heterocycle, heteroaryloxy, C₂–C₆ alkenyl, C₂–C₆ alkynyl, C₃–C₈ cycloalkyl, C₁–C₄ alkoxy, C₁–C₄ alkoxycarbonyl, phenyl(C₁–C₄ alkyl), substituted phenyl(C₁–C₄ alkyl), and benzofused C₄–C₈ cycloalkyl; and heterocycle is aromatic or non-aromatic 5 or 6 membered ring containing from 1 to 3 heteroatoms selected from the group consisting of nitrogen, oxygen, and sulfur, said ring being optionally benzofused and said ring or benzofused ring being optionally substituted with up to three substituents selected from the groups consisting of halo, C₁–C₄ alkoxy, C₁–C₄ alkyl, cyano, nitro, hydroxy, (C₁–C₄ alkyl)-S(O)ₙ—, and phenyl-S(O)ₙ—.

14. The method according to claim 13 where the mammal is a human.

15. The compound of claim 1 where A is hydrogen and R is methyl.

16. The compound of claim 4 where A is hydrogen and R is methyl.

17. The compound of claim 1 where R¹ is —NH—R²—R³, R² is C=O and R³ is substituted halophenyl.

18. A method for activating 5-F$_{1F}$ receptors in mammals comprising administering to a mammal in need of such activation an effective amount of a compound of formula I:

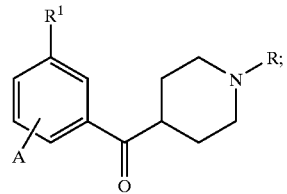

or a pharmaceutical acid addition salt thereof, where;

A is hydrogen, halo, NH₂, or —CF₃;

R is hydrogen, C₁–C₄ alkyl, C₃–C₆ alkenyl, C₃–C₆ alkynyl, or (C₁–C₆ alkyl)-Ar¹;

R¹ is —NH—R²—R³;

Ar, Ar¹, Ar², Ar³, and Ar⁴ are an optionally substituted phenyl or optionally substituted heteroaryl;

R² is —CO—;

R³ is;

wherein substituted phenyl is phenyl mono-substituted with a substituent selected from the group consisting of halo, nitro, cyano, amino, trifluoromethyl, trifluoromethoxy, phenyl, benzoyl, C₁–C₆ alkyl, C₁–C₆ alkoxy, (C₁–C₄ alkyl)S(O)ₙ, (C₁–C₄ alkyl)₂ amino, C₁–C₄ acyl, or two or three substituents independently selected from the group consisting of halo, nitro, trifluoromethyl, C₁–C₄ alkyl, and C₁–C₄ alkoxy;

n is 0, 1, or 2;

heteroaryl is an aromatic or benzofused aromatic 5 or 6 membered ring containing from 1 to 3 heteroatoms selected from the group consisting of nitrogen, oxygen and sulfur;

substituted heteroaryl is heteroaryl substituted with up to three substituents selected from the group consisting of halo, cyano, nitro, hydroxy, C₁–C₄ alkoxy, C₁–C₄ alkyl, (C₁–C₄ alkyl)-S(O)ₙ—, and phenyl-S(O)ₙ—;

substituted alkyl is alkyl substituted from 1 to 3 times independently with a substituent selected from the group consisting of halo, hydroxy, phenyl, 2-phenylethylen-1-yl, diphenylmethyl, naphthyl, substituted phenyl, aryloxy, heterocycle, heteroaryloxy, C₂–C₆ alkenyl, C₂–C₅ alkynyl, C₃–C₈ cycloalkyl, C₁–C₄ alkoxy, C₁–C₄ alkoxycarbonyl, phenyl(C₁–C₄ alkyl), substituted phenyl(C₁–C₄ alkyl), and benzofused C₄–C₈ cycloalkyl; and heterocycle is aromatic or non-aromatic 5 or 6 membered ring containing from 1 to 3 heteroatoms selected from the group consisting of nitrogen, oxygen, and sulfur, said ring being optionally benzofused and said ring or benzofused ring being optionally substituted with up to three substituents selected from the groups consisting of halo, C₁₋₄ alkoxy, C₁–C₄ alkyl, cyano, nitro, hydroxy, (C₁–C₄ alkyl)-S(O)ₙ—, and phenyl-S(O)ₙ—.

19. The method according to claim 18 where the mammal is a human.

* * * * *

UNITED STATES PATENT AND TRADEMARK OFFICE
CERTIFICATE OF CORRECTION

PATENT NO. : 6,777,428 B1
DATED : August 17, 2004
INVENTOR(S) : Krushinski, Jr. et al.

It is certified that error appears in the above-identified patent and that said Letters Patent is hereby corrected as shown below:

<u>Column 74,</u>
Line 22, reads "...$R^3$ is;" should read -- ...$R^3$ is $Ar^3$ --
Line 46, reads "...$C_2$-$C_5$ alkynyl,..." should read -- ...$C_2$-$C_6$ alkynyl,... --
Line 56, reads "...halo, $C_{1-4}$ alkoxy,..." should read -- ...halo, $C_1$-$C_4$ alkoxy,... --

Signed and Sealed this

Tenth Day of May, 2005

JON W. DUDAS
*Director of the United States Patent and Trademark Office*